US009861386B2

United States Patent
Wesley et al.

(10) Patent No.: US 9,861,386 B2
(45) Date of Patent: *Jan. 9, 2018

(54) HAIR RESTORATION

(71) Applicant: Pilofocus, Inc., New York, NY (US)

(72) Inventors: Carlos K. Wesley, New York, NY (US); Trevor K. Lewis, Lehi, UT (US)

(73) Assignee: PILOFOCUS, INC., New York, NY (US)

( * ) Notice: Subject to any disclaimer, the term of this patent is extended or adjusted under 35 U.S.C. 154(b) by 450 days.

This patent is subject to a terminal disclaimer.

(21) Appl. No.: 14/679,205

(22) Filed: Apr. 6, 2015

(65) Prior Publication Data

US 2015/0223840 A1     Aug. 13, 2015

Related U.S. Application Data

(63) Continuation of application No. 13/654,252, filed on Oct. 17, 2012, now Pat. No. 8,998,931.

(Continued)

(51) Int. Cl.
*A61B 17/14* (2006.01)
*A61B 17/34* (2006.01)
(Continued)

(52) U.S. Cl.
CPC ...... *A61B 17/3468* (2013.01); *A61B 1/00087* (2013.01); *A61B 1/313* (2013.01); *A61B 17/32002* (2013.01); *A61B 17/320016* (2013.01); *A61B 17/32053* (2013.01); *A61B 17/34* (2013.01); *A61B 90/50* (2016.02); *A61F 2/10* (2013.01); *A61B 17/32093* (2013.01);
(Continued)

(58) Field of Classification Search
CPC ........ A61B 2010/0208; A61B 10/0266; A61B 10/0233; A61B 10/02; A61B 17/32053; A61B 2017/00752; A61B 2018/00476; A61B 2017/00747; A61F 2/10

See application file for complete search history.

(56) References Cited

U.S. PATENT DOCUMENTS

| 4,476,864 A | 10/1984 | Tezel |
| 4,763,669 A | 8/1988 | Jaeger |

(Continued)

FOREIGN PATENT DOCUMENTS

| EP | 1642541 A1 | 4/2006 |
| GB | 2021467 A | 12/1979 |

(Continued)

OTHER PUBLICATIONS

Office Action with English translation for related South Korean Application No. 10-2012-7009817, dated Dec. 14, 2015 (13 pages).

(Continued)

*Primary Examiner* — Jonathan Miles
(74) *Attorney, Agent, or Firm* — Brinks Gilson & Lione; Ryan L. Marshall

(57) ABSTRACT

A surgical apparatus for hair removal surgery includes an extraction module, a visualization component and a bridging component. The extraction module includes independently controllable coring and clipping devices. The visualization component acts to align a target hair follicle with the extraction module. The extraction module also includes at least one independently controllable suction port. The instrument also includes a dissection module having a tissue separating device.

20 Claims, 39 Drawing Sheets

Related U.S. Application Data

(60) Provisional application No. 61/673,143, filed on Jul. 18, 2012, provisional application No. 61/547,898, filed on Oct. 17, 2011.

(51) Int. Cl.
| | | |
|---|---|---|
| *A61F 2/10* | (2006.01) | |
| *A61B 17/32* | (2006.01) | |
| *A61B 17/3205* | (2006.01) | |
| *A61B 1/00* | (2006.01) | |
| *A61B 1/313* | (2006.01) | |
| *A61B 90/50* | (2016.01) | |
| *A61B 17/3209* | (2006.01) | |
| *A61B 17/00* | (2006.01) | |
| *A61B 90/00* | (2016.01) | |

(52) U.S. Cl.
CPC ............... *A61B 2017/00752* (2013.01); *A61B 2017/32004* (2013.01); *A61B 2090/378* (2016.02); *A61B 2217/005* (2013.01); *F04C 2270/041* (2013.01)

(56) References Cited

U.S. PATENT DOCUMENTS

| | | |
|---|---|---|
| 5,133,360 A | 7/1992 | Spears |
| 5,133,722 A | 7/1992 | Avrahami et al. |
| 5,135,531 A | 8/1992 | Shiber |
| 5,368,014 A | 11/1994 | Anapliotis et al. |
| 5,391,166 A | 2/1995 | Eggers |
| 5,439,475 A | 8/1995 | Bennett |
| 5,445,615 A | 8/1995 | Yoon |
| 5,472,439 A | 12/1995 | Hurd |
| 5,478,351 A | 12/1995 | Meade et al. |
| 5,535,759 A | 7/1996 | Wilk |
| 5,601,601 A | 2/1997 | Tal et al. |
| 5,618,303 A | 4/1997 | Marlow et al. |
| 5,630,782 A | 5/1997 | Adair |
| 5,665,100 A | 9/1997 | Yoon |
| 5,676,678 A | 10/1997 | Schad |
| 5,676,680 A | 10/1997 | Lim |
| 5,782,851 A | 7/1998 | Rassman |
| 5,782,853 A | 7/1998 | Zeevi |
| 5,788,651 A | 8/1998 | Weilandt |
| 5,792,163 A | 8/1998 | Hitzig |
| 5,817,120 A | 10/1998 | Rassman |
| 5,823,971 A | 10/1998 | Robinson et al. |
| 5,827,297 A | 10/1998 | Boudjema |
| 5,895,403 A | 4/1999 | Collinsworth |
| 5,922,000 A | 7/1999 | Chodorow |
| 5,984,936 A | 11/1999 | Mangubat et al. |
| 6,027,512 A | 2/2000 | Bridges |
| 6,059,719 A | 5/2000 | Yamamoto et al. |
| 6,352,503 B1 | 3/2002 | Matsui et al. |
| 6,419,627 B1 | 7/2002 | Ben Nun |
| 6,500,170 B2 | 12/2002 | Palmer et al. |
| 6,544,259 B1 | 4/2003 | Tsaliovich |
| 6,572,625 B1 | 6/2003 | Rassman |
| 6,585,746 B2 | 7/2003 | Gildenberg |
| 6,620,158 B2 | 9/2003 | Ronci |
| 7,130,717 B2 | 10/2006 | Gildenberg |
| 7,156,856 B2 | 1/2007 | Feller |
| 7,261,721 B2 | 8/2007 | Feller |
| 7,329,252 B1 | 2/2008 | Yamazaki et al. |
| 7,517,321 B2 | 4/2009 | McCullough et al. |
| 7,621,933 B2 | 11/2009 | Bodduluri |
| 7,621,934 B2 | 11/2009 | Bodduluri |
| 7,627,157 B2 | 12/2009 | Qureshi |
| 7,727,164 B2 | 6/2010 | Cicenas et al. |
| 7,806,121 B2 | 10/2010 | Bodduluri |
| RE42,381 E | 5/2011 | Gildenberg |
| RE42,437 E | 6/2011 | Gildenberg |
| RE42,438 E | 6/2011 | Gildenberg |
| 7,962,192 B2 | 6/2011 | Bodduluri |
| 8,048,090 B2 | 11/2011 | Qureshi |
| 8,066,717 B2 | 11/2011 | DuBois |
| 8,104,480 B2 | 1/2012 | Bodduluri |
| 8,128,639 B2 | 3/2012 | Tippett |
| 8,133,237 B2 | 3/2012 | Oostman, Jr. |
| 8,133,247 B2 | 3/2012 | Bodduluri et al. |
| 8,317,804 B1 | 11/2012 | Rassman et al. |
| 8,454,627 B2 | 6/2013 | Bodduluri et al. |
| 8,690,894 B2 | 4/2014 | Bodduluri et al. |
| 8,998,931 B2 | 4/2015 | Wesley et al. |
| 2002/0042623 A1 | 4/2002 | Blatter et al. |
| 2002/0103500 A1 | 8/2002 | Gildenberg |
| 2003/0040706 A1 | 2/2003 | Kuracina et al. |
| 2003/0097143 A1 | 5/2003 | Mittelstaedt |
| 2003/0097144 A1 | 5/2003 | Lee |
| 2003/0120298 A1 | 6/2003 | Gildenberg |
| 2003/0212415 A1 | 11/2003 | Karasiuk |
| 2003/0233114 A1 | 12/2003 | Merboth |
| 2004/0049206 A1 | 3/2004 | Rassman |
| 2004/0092924 A1 | 5/2004 | Vasa |
| 2004/0097973 A1 | 5/2004 | Loshakove et al. |
| 2005/0049622 A1 | 3/2005 | Mittelstaeot |
| 2005/0177142 A1 | 8/2005 | Jay |
| 2005/0216035 A1 | 9/2005 | Kraus et al. |
| 2005/0267506 A1 | 12/2005 | Harris |
| 2006/0142741 A1 | 6/2006 | Jay |
| 2006/0161179 A1 | 7/2006 | Kachenmeister |
| 2006/0178677 A1 | 8/2006 | Brinson |
| 2006/0200040 A1 | 9/2006 | Weikel et al. |
| 2006/0259102 A1 | 11/2006 | Slatkine |
| 2007/0078466 A1 | 4/2007 | Bodduluri |
| 2007/0078473 A1 | 4/2007 | Bodduluri et al. |
| 2007/0106307 A1 | 5/2007 | Bodduluri |
| 2007/0122387 A1 | 5/2007 | Cochran |
| 2007/0128172 A1 | 6/2007 | Yoshizato |
| 2007/0156164 A1 | 7/2007 | Cole |
| 2007/0213741 A1 | 9/2007 | Cole |
| 2007/0255293 A1 | 11/2007 | Corre |
| 2007/0293884 A9 | 12/2007 | Cole |
| 2008/0033410 A1 | 2/2008 | Rastegar et al. |
| 2008/0033455 A1 | 2/2008 | Rassman |
| 2008/0051805 A1 | 2/2008 | Pinchuk |
| 2008/0051806 A1 | 2/2008 | Cole |
| 2008/0082114 A1 | 4/2008 | McKenna et al. |
| 2008/0091225 A1 | 4/2008 | Cole et al. |
| 2008/0097458 A1 | 4/2008 | Donahoe et al. |
| 2008/0177287 A1 | 7/2008 | Rassman |
| 2008/0186496 A1 | 8/2008 | Leveque |
| 2008/0200861 A1 | 8/2008 | Shalev et al. |
| 2008/0215039 A1 | 9/2008 | Slatkine et al. |
| 2008/0234697 A1 | 9/2008 | DuBois |
| 2008/0234698 A1 | 9/2008 | Oostman |
| 2009/0005765 A1 | 1/2009 | Oostman |
| 2009/0012536 A1 | 1/2009 | Rassman et al. |
| 2009/0052738 A1 | 2/2009 | Qureshi |
| 2009/0088776 A1 | 4/2009 | Harris |
| 2009/0192456 A1 | 7/2009 | Lee et al. |
| 2009/0240261 A1 | 9/2009 | Drews |
| 2009/0306498 A1 | 12/2009 | Bodduluri |
| 2009/0306680 A1 | 12/2009 | Qureshi |
| 2010/0080415 A1 | 4/2010 | Qureshi |
| 2010/0080417 A1 | 4/2010 | Qureshi |
| 2010/0082042 A1 | 4/2010 | Drews |
| 2010/0125287 A1 | 5/2010 | Cole |
| 2010/0166719 A1 | 7/2010 | Yoshizato |
| 2010/0217236 A1 | 8/2010 | Gill |
| 2010/0262129 A1 | 10/2010 | Roy |
| 2011/0046639 A1 | 2/2011 | Giotis |
| 2011/0060321 A1 | 3/2011 | Chandler |
| 2011/0160746 A1 | 6/2011 | Umar |
| 2011/0178533 A1 | 7/2011 | Oostman |
| 2011/0224693 A1 | 9/2011 | Bodduluri |
| 2011/0245845 A1 | 10/2011 | Oostman |
| 2011/0319921 A1 | 12/2011 | Giotis |
| 2012/0010631 A1 | 1/2012 | DuBois |
| 2012/0039516 A1 | 2/2012 | Qureshi |
| 2012/0041430 A1 | 2/2012 | Anderson |
| 2012/0041451 A1 | 2/2012 | Bodduluri |
| 2012/0215231 A1 | 8/2012 | Wesley |

(56) References Cited

U.S. PATENT DOCUMENTS

| | | |
|---|---|---|
| 2013/0096600 A1 | 4/2013 | Wesley et al. |
| 2013/0190776 A1 | 7/2013 | Zhang et al. |
| 2013/0226213 A1 | 8/2013 | Kim et al. |
| 2013/0304090 A1 | 11/2013 | Oostman et al. |
| 2014/0236181 A1 | 8/2014 | Wesley et al. |
| 2014/0243870 A1 | 8/2014 | Wesley et al. |
| 2015/0012012 A1 | 1/2015 | Wesley et al. |
| 2015/0012013 A1 | 1/2015 | Wesley et al. |
| 2015/0223840 A1 | 8/2015 | Wesley et al. |

FOREIGN PATENT DOCUMENTS

| | | |
|---|---|---|
| JP | 59-114511 | 7/1984 |
| JP | 64-080335 | 3/1989 |
| JP | 03-086315 | 4/1991 |
| JP | 09-215656 | 8/1997 |
| JP | 2000-014631 A | 1/2000 |
| JP | 2000-037348 A | 2/2000 |
| JP | 2001-511393 A | 8/2001 |
| JP | 2008-502437 A | 1/2008 |
| JP | 2011-516169 A | 5/2011 |
| KR | 2007-0037577 A | 4/2007 |
| WO | WO 99/05997 A1 | 2/1999 |
| WO | WO 01/35125 A1 | 5/2001 |
| WO | WO 2005/109799 A2 | 11/2005 |
| WO | WO 2007/041267 A2 | 4/2007 |
| WO | WO 2007/087463 A2 | 8/2007 |
| WO | WO 2008/024954 A2 | 2/2008 |
| WO | WO 2008/027829 A2 | 3/2008 |
| WO | WO 2009/083741 A1 | 7/2009 |
| WO | WO 2009/123635 A1 | 10/2009 |
| WO | WO 2009/146068 A1 | 12/2009 |
| WO | WO 2010/039413 A1 | 4/2010 |
| WO | WO 2010/041089 A1 | 4/2010 |
| WO | WO 2010/057018 A2 | 5/2010 |
| WO | WO 2010/131270 A1 | 11/2010 |
| WO | WO 2011/035125 A1 | 3/2011 |
| WO | WO 2011/082130 A2 | 7/2011 |
| WO | WO 2011/123218 A1 | 10/2011 |
| WO | WO 2013/059349 A1 | 4/2013 |
| WO | WO 2014/182941 A1 | 11/2014 |

OTHER PUBLICATIONS

Notification of Reasons for Rejection with English translation for related Japanese Application No. 2014-537187, dated Jan. 5, 2016 (4 pages).
Office Action for related U.S. Appl. No. 14/273,009, dated Sep. 7, 2016 (40 pages).
Office Action for related U.S. Appl. No. 14/273,058, dated Aug. 25, 2016 (37 pages).
Office Action for related U.S. Appl. No. 14/273,105, dated Sep. 16, 2016 (41 pages).
Third Office Action, and English language translation thereof, in Chinese Application No. 201080052239.3, dated Jul. 1, 2015, 17 pages.
Chinese Office Action (English Translation) for related Chinese Application No. 201080052239.3, dated Apr. 11, 2014 (9 pages).
Final Office Action for related U.S. Appl. No. 13/496,905 with related technology, dated Nov. 28, 2014 (17 pages).
International Preliminary Report on Patentability for International Application No. PCT/US2012/060653, dated Apr. 22, 2014 (8 pages).
International Search Report and Written Opinion for corresponding International Application No. PCT/US2014/037358, dated Oct. 27, 2014 (15 pages).
Invitation to Pay Additional Fees and, Where Applicable, Protest Fee for corresponding International Application No. PCT/US2014/037358, dated Sep. 4, 2014 (6 pages).
Notification of Reasons for Rejection (English translation) for related Japanese Application No. 2012-529930, dated Apr. 15, 2014 (6 pages).
Patent Examination Report No. 1 for Australian Application No. 2014203223, dated Apr. 30, 2015 (3 pages).
Second Office Action for corresponding Chinese Application No. 201080052239.3, dated Nov. 19, 2014 (15 pages).

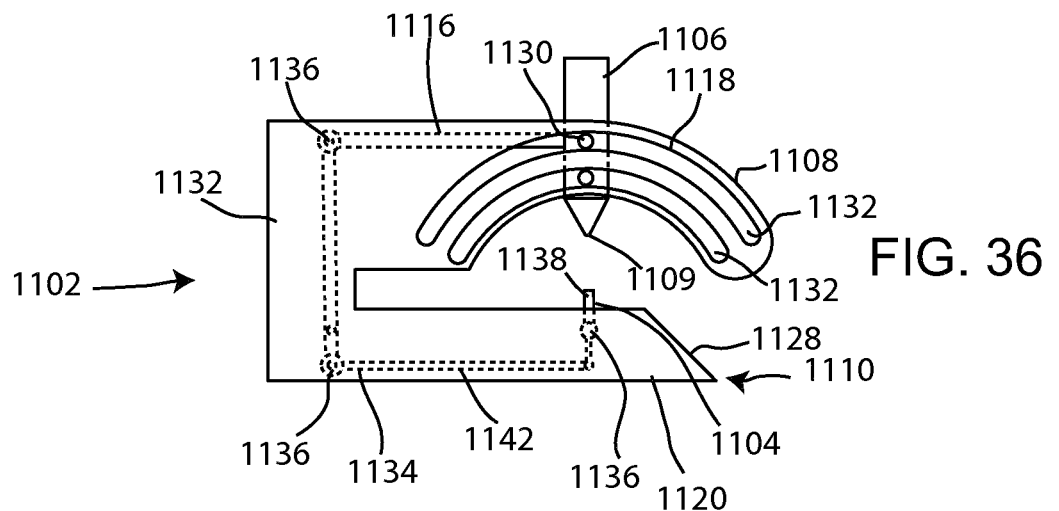
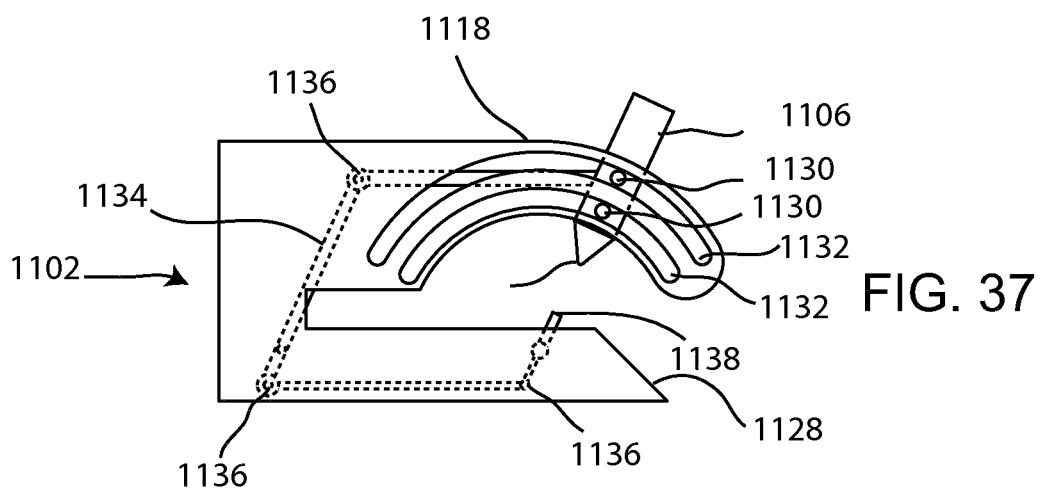
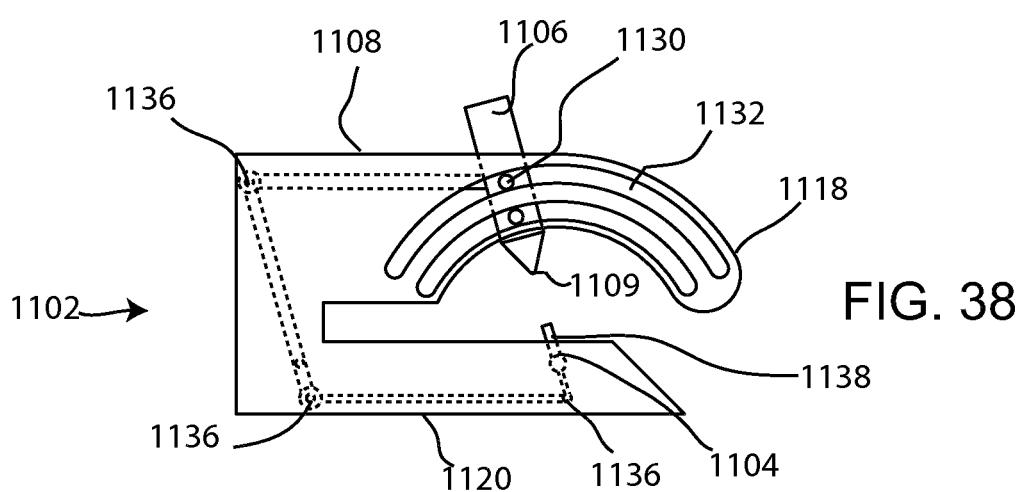

HAIR RESTORATION

RELATED APPLICATION

The present patent application is a continuation of and claims the benefit of priority to U.S. Non-Provisional patent application Ser. No. 13/654,252, filed Oct. 17, 2012, and entitled "HAIR RESTORATION", which issued as U.S. Pat. No. 8,998,931 on Apr. 7, 2015, which in turn claims the benefit of priority to U.S. Provisional Patent Application No. 61/547,898, filed Oct. 17, 2011, entitled "ENDOSCOPIC HAIR RESTORATION" and to U.S. Provisional Patent Application No. 61/673,143, filed Jul. 18, 2012, entitled "HAIR RESTORATION." The entire contents of each application are incorporated herein by reference.

BACKGROUND

The present disclosure relates to an instrument that may be used for Hair Restoration Surgery (HRS) or any subdermal tissue removal procedure without altering the integrity of the overlying skin surface. The surgical method of donor follicle removal in HRS is based on the principal of "donor dominance", wherein the region of the scalp in which the hair is destined to persist throughout a person's lifetime, known as the "donor area" will continue to grow in the same fashion, when transplanted to the "recipient area", or the scalp zone of non-permanent hair growth.

Original HRS techniques included the excision of large punch grafts from the donor area and transplantation to the recipient area. Utilization of these large grafts was necessary in order to ensure hair survival after transplantation. Smaller grafts, or implantation into smaller recipient sites, were often not feasible due to the low graft viability secondary to decreased blood perfusion of transplanted grafts. While this large-graft method enabled transplanted graft growth within the recipient area, the grafts often had an unnatural, "pluggy" appearance, and the punched-out scars in the donor area left an unattractive buckshot-type pattern in the back of a patient's head.

To overcome these methodical and aesthetic shortcomings of many original HRS techniques, an alternative method for donor hair harvesting was proposed: the strip harvest technique. This alternative approach involved the following procedural steps: removing a strip of hair-follicle bearing skin from the donor region, suturing the donor wound closed, dissecting out each individual follicle or cluster of follicles (a.k.a. a "follicular unit", FU), and transplanting each individual FU separately in the recipient area. Each FU may contain one or more individual hair follicles and can be defined based on the naturally-occurring arrangement of a bulb region. An FU may be classified based on its caliber and the quantity of hairs it contains as a single-haired FU, a fine-single-haired FU, a double-haired FU, a fine double-haired FU, a triple-haired FU, or a follicular family containing four or more intact hair follicles.

The approach, known as "micrografting" or "follicular unit transplanting" (FUT), helped to create a more natural and less "pluggy" appearance in the recipient area than that resulting from the large grafts. Furthermore, this new approach left only a linear scar in the donor area, rather than a more obvious buckshot pattern.

In order to achieve a maximum number of grafts via the "micrografting" technique, many patients requested wider donor strip removal which would, in turn, yield more donor hair follicles. A consequence of this more aggressive approach is that patients are increasingly left with relatively large (2-10 mm) and obvious linear scars in the donor portion of their head. To reduce or eliminate this aesthetically displeasing result, a process known as Follicular Unit Extraction (FUE) was developed. In FUE, each individual follicular unit is meticulously punched out from the donor area with a small biopsy punch, and then transplanted into the recipient area. This differs from the original approach to HRS in that FUE involves the transfer of only individual FU's, rather than large (4-5 mm) punch grafts.

However, several disadvantages persisted with the advent of FUE: a high percentage (up to 40%) of hairs are transected (thus, limiting their survival), a moth-eaten scarring pattern often still remains (though to a lesser degree than seen with the original, larger punch grafts) from where FUs are extracted, and a considerable number of patients (up to 30%) are not candidates for FUE based on their hair characteristics (e.g. light color or considerable and unpredictable curl beneath the skin surface) that present undue challenges for the surgeon.

The technique described herein allows for: 1) the isolation of an intact hair follicle with maximal tissue (both dermal and subcutaneous) surrounding the stem cell-containing portion of the follicle without traumatizing the overlying skin surface; and 2) eliminates the stigma of any apparent scar in the donor area from which the hair is harvested.

A challenge associated with extracting/harvesting tissue that includes essential portions beneath the skin surface often pertains to determination of the location, depth, and position of the desired tissue. Without cutting or altering the integrity of the overlying skin surface, obtaining the desired tissue segment beneath the skin is especially difficult. In order to overcome these challenges, a device is disclosed herein to enable a user to 1) manipulate a visualization device located outside of the skin surface to identify a target tissue, and 2) harvest tissue located beneath the skin surface based on the information provided by the visualization device. Movement of the visualization device and the internal issue extraction device are directly tied to the movements of the operator performing each movement outside of the skin surface.

Without cutting or altering the overlying skin surface, the design described herein enables a precisely-controlled extraction/harvest of desired tissue that accounts for the borders of the desired tissue, the angle and direction of the tissue (e.g. hair follicle) as it is positioned beneath the skin surface, and the depth of penetration of the desired tissue all while effectively avoiding inclusion of undesirable surrounding tissue in the harvest or injuring vital vessels or nerve plexes in the process.

The direct association between the visualization/manipulation of a probe located outside of the body and the extraction/harvesting module located within the body that approaches, but does not directly touch, the outerlying probe enables this unique achievement.

BRIEF SUMMARY

In an aspect of the technology for a hair restoration system, the system includes a body, wherein the body includes a handle portion, a bridging component and a distal arm, wherein the bridging component is between the handle portion and the distal arm. The system also includes a dissection module removably coupled to the body, the dissection module having a tissue separating device. The system also includes an extraction module, wherein the extraction module includes a coring component, a plurality of cutting features, and at least one tissue removal port, wherein the tissue removal port is carried by the distal arm, wherein the extraction module includes a central extraction axis.

In another example of the system, the central extraction axis is perpendicular to a first axis, wherein the extraction module is pivotable around the first axis to an aligned orientation with a target tissue.

In another example of the system, the system includes an external reference module.

In yet another example of the system, the external reference module is a visualization component, wherein the visualization component includes a central visualization axis.

In yet another example of the system, the visualization module is always/permanently aligned with the central extraction axis of the extraction module.

In yet another example of the system, the visualization component includes an ultrasound visualization device.

In yet another example of the system, the external reference module has an imaging system, wherein the imaging system includes a light source for illuminating a target, wherein the imaging system further includes a viewing port for receiving an image of the target.

In yet another example of the system, the system includes a plurality of independently controllable tissue removal implements, wherein each tissue removal implement is coupled to a corresponding suction port.

In yet another example of the system, the system includes a plurality of control modules, wherein each control module is configured to control the operation of a corresponding one of the suction ports. In yet another example of the system, the removal port is a portion of a tissue removal pathway, wherein the tissue removal pathway is in fluid communication with a tissue reservoir.

In yet another example of the system, the system includes a motor unit, wherein the motor unit has a motor shaft, wherein the motor shaft is in communication with a gear system.

In yet another example of the system, the dissection module includes a blade.

In yet another example of the system, the system includes a dermal shifter, wherein the dermal shifter has a plurality of needles, wherein the plurality of needles are actuatable to align a target tissue with the central extraction axis.

In another aspect of the technology for a hair restoration system, the system includes a body, wherein the body includes a handle portion and a distal portion. The system also includes an extraction module, wherein the extraction module has a tissue extraction component and a tissue removal component, wherein the tissue extraction component has a central extraction axis, a cannulated element and a plurality of cutting features, wherein the tissue removal component is a portion of a tissue removal pathway, wherein the extraction module is carried by the distal portion, wherein an activation component is in communication with the extraction module.

In another example of the system, the cannulated element has a coring cannula and a clipping cannula, wherein the clippling cannula includes the plurality of cutting features.

In yet another example of the system, the system includes a dissection module, wherein the dissection module is maneuverable to separate tissue layers to create a cavity.

In yet another example of the system, the system includes an external reference module, wherein the external reference module is configured to be manipulated to identify and gather information about a target tissue, wherein the external reference module is external to an exterior tissue surface.

In yet another example of the system, the extraction module is maneuverable within the cavity along an interior tissue surface.

In yet another example of the system, the external reference module is communicably attached to the extraction module.

In yet another example of the system, the extraction module is configured to subcutaneously extract a hair follicle.

In yet another example of the system, the system includes an extraction trigger and an alignment adjuster, wherein the alignment adjuster is carried by a cable that is in communication with the extraction module, wherein when the alignment adjuster is actuated, the central extraction axis is pivotable about a first axis to align with a target tissue, wherein when the extraction trigger is actuated, the extraction module removes the target tissue along the tissue removal pathway.

In an example of a method for hair follicle extraction, the method includes creating an incision in a layer of tissue, separating the layer of tissue from an underlying layer of tissue to create a cavity, inserting a distal arm of an instrument into the cavity, wherein the distal arm carries an extraction module, wherein the extraction module has a central extraction axis, positioning the instrument such that the visualization module is close to a superficial surface of the tissue, wherein the visualization module and the extraction module are always aligned, using the visualization module to identify a target piece of tissue, and actuating the instrument such that the extraction module removes the target piece of tissue.

In another example of the method, extraction module further includes a suction port, wherein when the target piece of tissue is removed, the target piece of tissue is carried along a removal pathway through the suction port.

In yet another example of the method, the method further includes obtaining an image of exterior skin tissue from outside the cavity.

In yet another example of the method, the image is an ultrasound image.

In yet another example of the method, the method further includes applying a suction force to the target piece of tissue through the suction port, wherein applying suction to the target piece of tissue includes controlling the suction port via at least one of a mechanical control apparatus and an electronic control apparatus.

In yet another example of the method, the method further includes removing the target piece of tissue along a removal pathway, wherein the removal pathway is in fluid communication with at least one tissue isolation container.

In yet another example of the method, the isolation container has a sensor, wherein the sensor identifies the removed target piece of tissue.

In yet another example of the method, the method further includes aligning the central extraction axis with the target piece of tissue.

In yet another example of the method, the instrument includes an extraction trigger and an alignment adjuster, wherein the alignment adjuster is carried by a cable that is in communication with the extraction module. The method further includes actuating the alignment adjuster to align the central extraction axis with the target piece of tissue, wherein the method further includes actuating the extraction trigger to advance the extraction module towards the target piece of tissue and to cut the target piece of tissue away from surrounding tissue.

BRIEF DESCRIPTION OF THE DRAWINGS

FIG. 36 is a side view of a working end of an instrument for follicular unit extraction with an external reference rod in a first position;

FIG. 37 is a side view of a working end of an instrument for follicular unit extraction with an external reference rod in a second position;

FIG. 38 is a side view of a working end of an instrument for follicular unit extraction with an external reference rod in a third position;

DETAILED DESCRIPTION

Figure 1A:
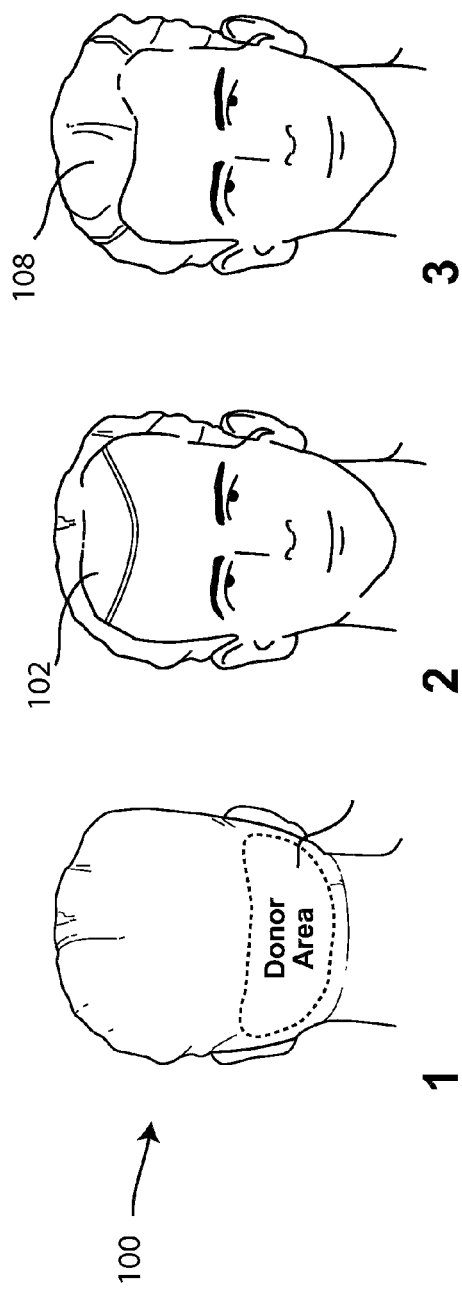
FIGS. 1A and 1B are top, front, side, and back views of a patient's head.
Figure 1B:
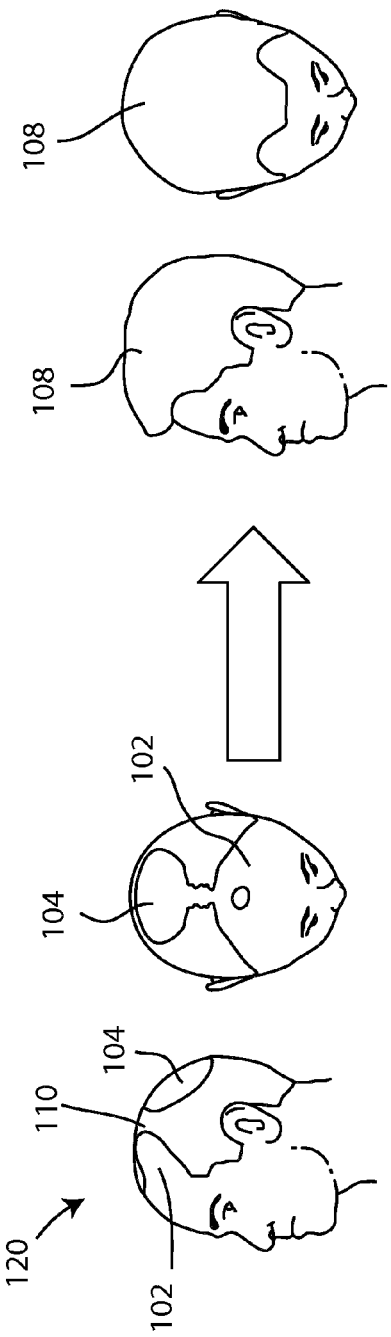

Referring to FIGS. 1A and 1B, a patient 100, 120 may experience hair loss in patterns consistent with androgenetic alopecia (male pattern baldness or female pattern hair loss) or in more random (focal or diffuse) patterns as seen from various non-androgenetic pathologies such as cicatricial alopecia. The most commonly-affected areas in androgenetic alopecia are a frontal third 102, a midscalp 110, and a vertex (or crown) 104. Although hair loss frequently involves the scalp, it can occur in other areas of the body. Surgical hair restoration harvests hair follicles from a donor area 106 and transplants the intact follicles to the regions of hair loss which include, but are not limited to, regions 102, 110, and 104.

After full growth of the transplanted follicles has been achieved, the post-operative patient enjoys a fuller head of hair 108, thicker eyebrows, fuller eyelashes, or even more substantial facial or body hair. In endoscopic surgical hair restoration, or piloscopy, individual intact hair follicles or follicular units are removed with minimal or no disruption of the stratum corneum 210 by an endoscopic device inserted beneath the scalp.

Figure 2:
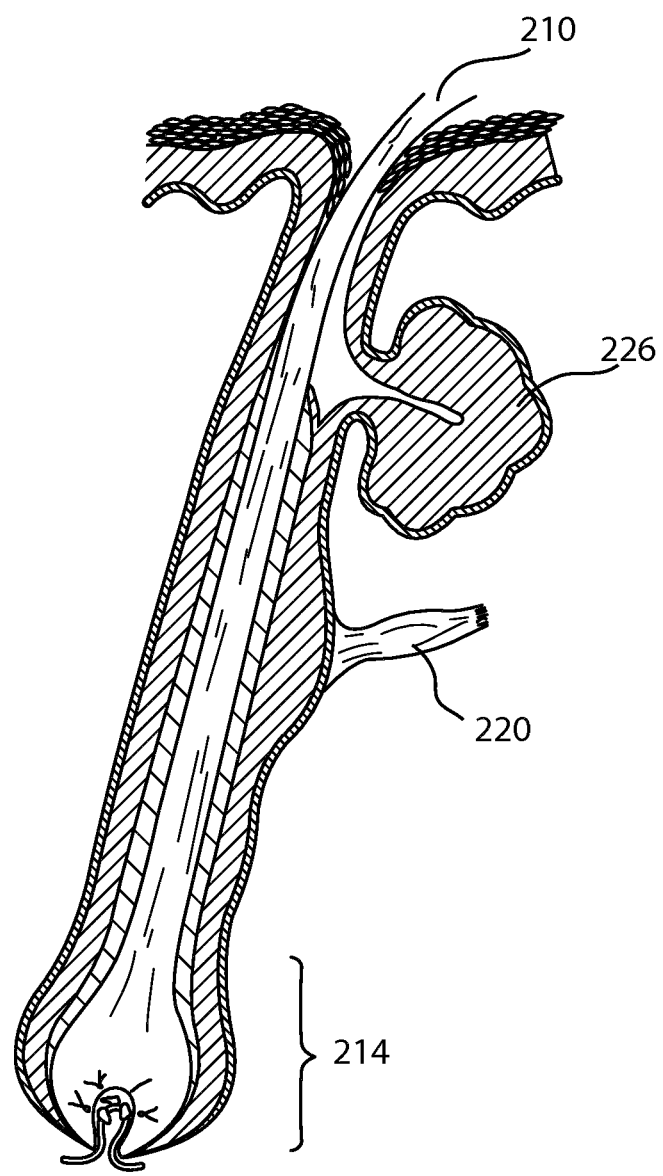
FIG. 2 is a detailed illustration of an intact hair follicle.

Referring to FIG. 2, a cross-section of a hair follicle 202 shows the native tissue surrounding a hair follicle 202. Spanning three separate layers of the skin—an epidermis 204, a dermis 206, and a fat-containing, subcutaneous layer 208—the follicle 202 protrudes through the skin surface at the most superficial layer of the epidermis 204, the stratum corneum 210. The intact hair follicle 202 includes the components that enable self-renewal of the follicle after it is transplanted into viable autologous tissue. The two critical regions in which stem cells abound are a bulge region 212 located near an erector pilli muscle 226 and a follicular bulb 214 which contains a dermal papilla 216.

Communication between these two stem-cell enriched areas promotes hair follicle regeneration. Other components of an intact hair follicle 202 include a hair shaft 218, an inner root sheath 222, an outer root sheath 224, and a sebaceous gland 228.

In endoscopic surgical hair restoration, or piloscopy, each hair follicle 202 or follicular unit (FU) is approached and removed from beneath the surface of the skin. Specifically, each individual follicle may be visualized from a uniform plane 230 that is surgically created within the subcutaneous layer 208 about 1-5 mm deep to the follicular bulbs 214 and then excised with a small punch blade, as discussed in greater detail below. Excision may incorporate a 1-7 mm portion of peri-follicular subcutaneous tissue deep to the follicular bulb 214 as well as the hair follicle 202 in its entirety while leaving intact the stratum corneum 210 that lies superficial to the native tissue that originally surrounded the extracted follicle. The plane 230 may be a tissue cleavage plane or a flat geometric plane.

Figure 3:
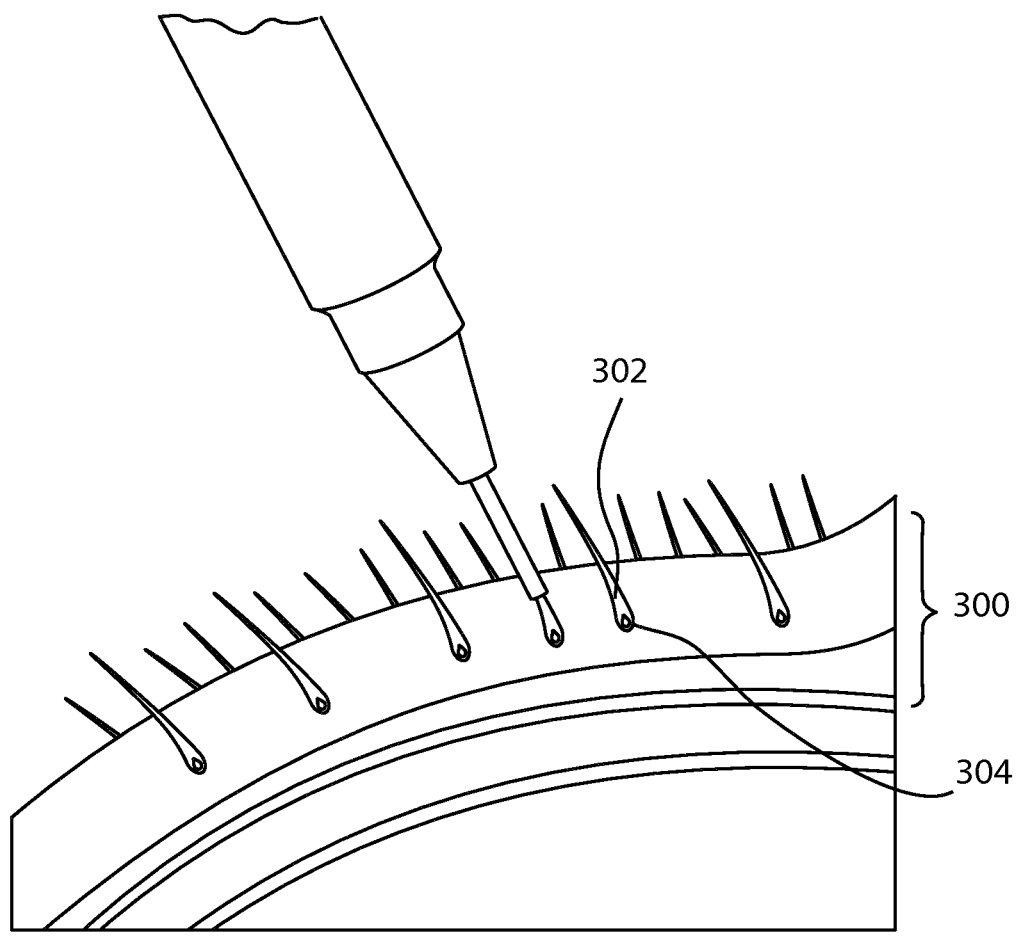
FIG. 3 is a cross-section view of a scalp undergoing preparation for hair restoration surgery.
Figure 4:
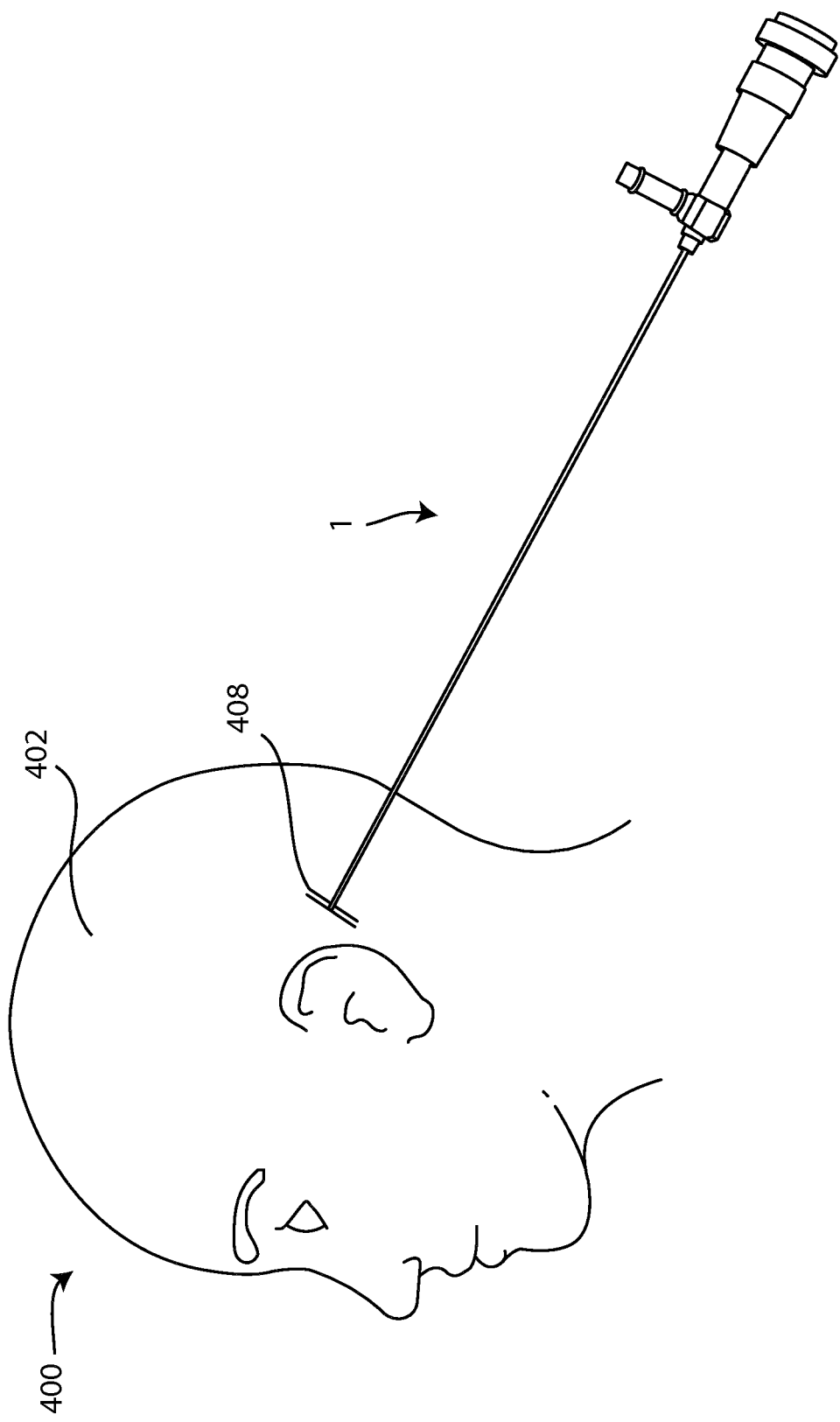
FIG. 4 is a side view of a patient's head with an endoscope being introduced through an incision.
Figure 5C:
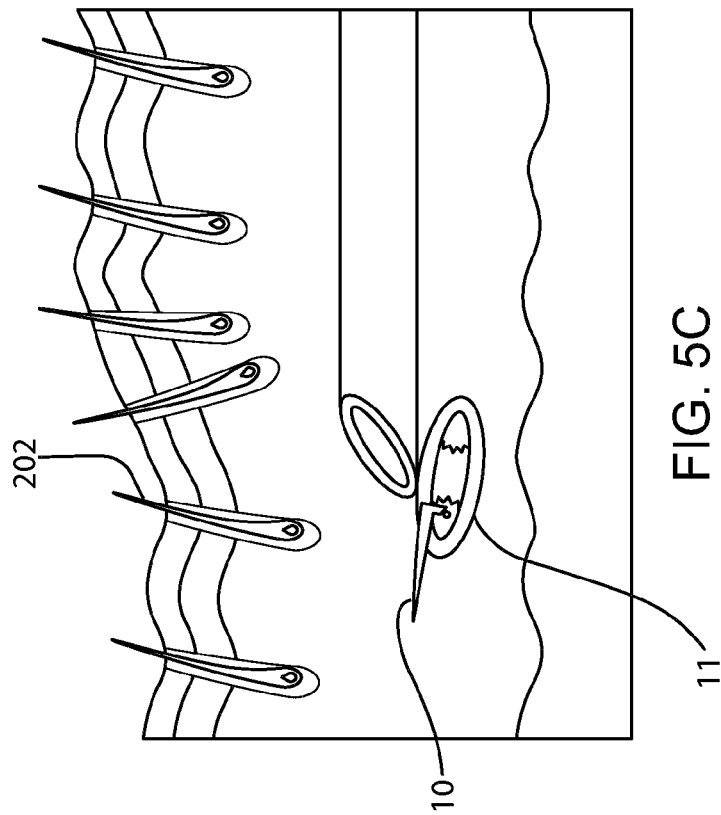
FIGS. 5A-5C are cross-sectional views of a blade being used to create a visual cavity.
Figure 5B:
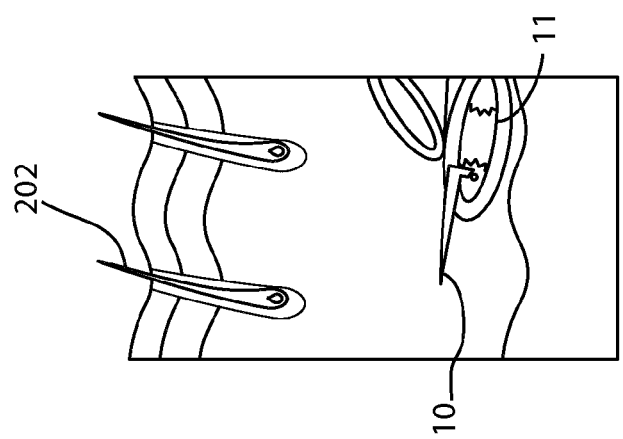
Figure 5A:
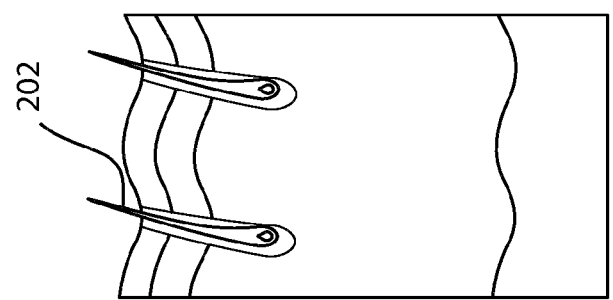

Referring to FIG. 3, prior to the initiation of hair restoration surgery, sterile saline tumescence (typically about 1-10 mL/cm2) may be applied to a scalp 300 at two levels within the area from which hair follicles will be harvested: a first superficial level 302 approximately 2 mm below the skin surface and a second deep level 304 approximately 4-5 mm deep to the skin surface. The saline tumescence may serve a number of purposes in tissue manipulation. In superficial tissue, it may be used as a form of anesthesia. Together, the tumescent applications at superficial level 302 and deep level 304 may facilitate extraction of the follicular bulb from its native surrounding tissue. The first superficial layer of tumescence 302 may help distance the follicle of interest from neighboring follicles and increases skin turgor in patients with otherwise easily broken tissue. The second tumescent layer 304 may distance the dermal papilla 216 from any nearby vascular and nerve plexus deep to the follicle bulbs, thus helping define plane 230 in which a visual cavity can subsequently be created.

Saline tumescence may also serve to align the desired hair follicles into a more predictable orientation (e.g., perpendicular) with respect to the overlying skin surface.

Referring to FIGS. 4 and 5A-C, an endoscopic approach to follicular harvesting may use an endoscope 1, which may also be referred to as a piloscope, to dissect a plane of subcutaneous tissue deep to hair follicles in a scalp 402 of a patient 400. A single, unilateral full-thickness 1 cm incision 408 may be made in a post-auricular zone of scalp 402. Alternative size and shape incisions may be made. Multiple incisions may also be made.

Figure 6:
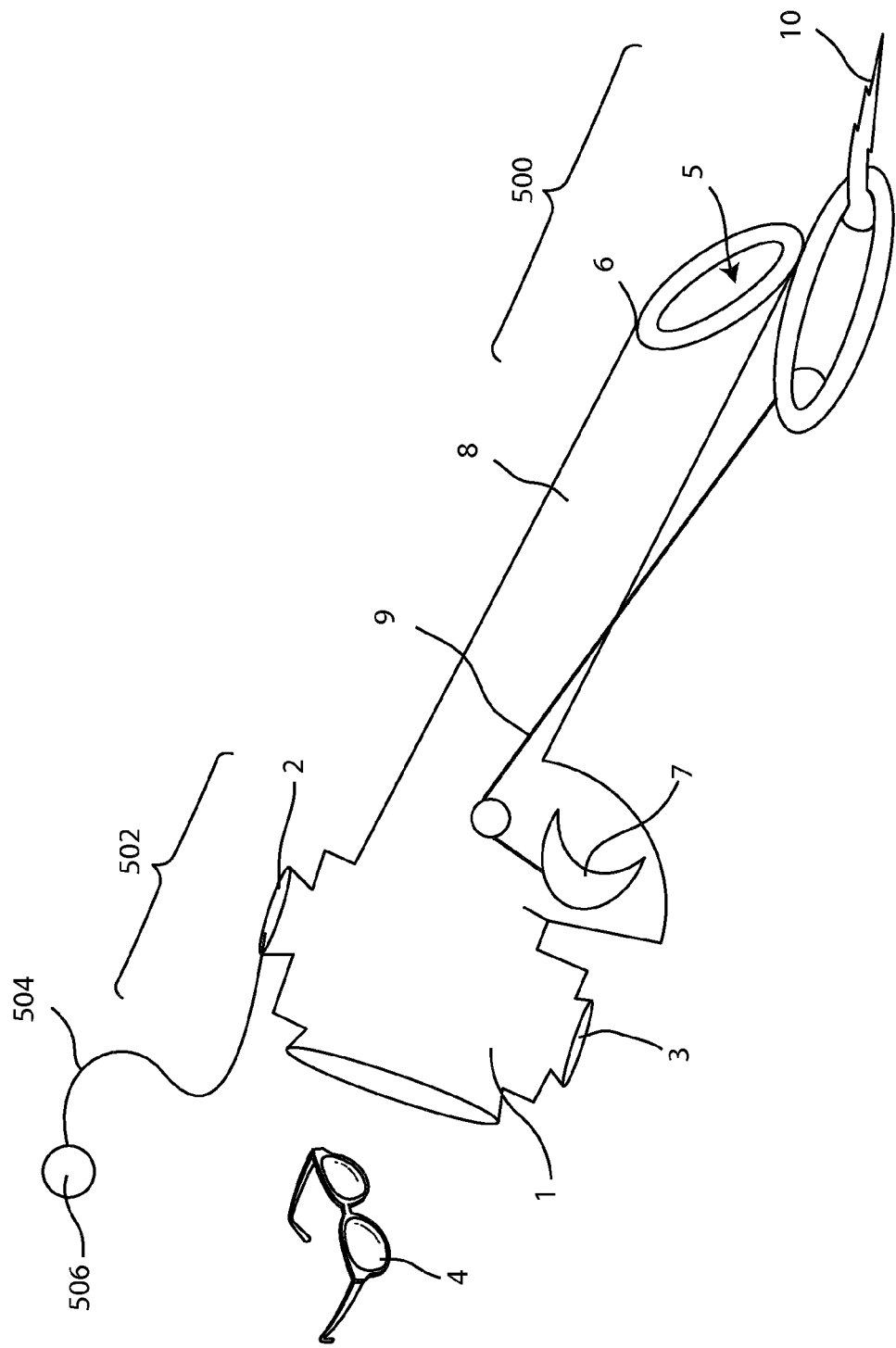
FIG. 6 is a side view of an endoscope including a distal dissection blade attachment.

In the example shown in FIG. 6, a 0.5 mm cannulated metal trocar 8 containing a 0.4 mm endoscope 1 attached to a thin linear cutting blade 10 is inserted into incision 408 to dissect a plane of sub-follicular subcutaneous tissue, creating a layer of separation deep to the follicular bulbs. The dissection may be also be made using a blunt module or instrument.

The layer of separation is, for instance, 1-5 mm deep to the follicular bulbs. In some embodiments, the layer of separation is 1-3 mm deep to the follicular bulbs so as to enable close visual proximity to the follicular bulbs without altering their structural integrity. In general, the depth of the layer of separation is such that an operator of endoscope 1 can visualize and separate connective tissue beneath the plane of the follicular bulbs while minimizing trauma to the blood vessels and nerve vessels in the vicinity.

The layer of separation may then be converted to an enlarged visual cavity in which an operator of endoscope 1 may observe the deep structures, such as the bulb 214 of each FU, prior to excising the intact FU from its native surrounding tissue for subsequent transplantation into the surgical recipient area (e.g., regions 102, 110 and 104 of FIG. 1A).

For example, the enlarged visual cavity may be created by humidified insufflation, external traction, or balloon expansion.

Referring to FIG. 6, cutting blade 10 may be attached to a distal end 500 of endoscope 1 and may be manipulated by an operator via a hand-held engagement device (e.g., a trigger) 7 at a proximal end 502 of endoscope 1. The cutting blade 10 may alternatively be placed on another location on endoscope 1. Cutting blade 10 may typically be about 0.5-6.0 mm in length. Trigger 7 may control cutting blade 10 to move rotationally, facilitating the cutting and separation of soft subcutaneous adipose tissue. When activated, cutting blade 10 may advance dissection by pushing forward and downward in a clockwise or counter-clockwise fashion away from distal end 500 of endoscope 1. In addition to the forward and downward motion that advances cutting blade 10 during dissection, an operating lever including a tape 11, a driver wheel 12, and a steering wheel 13 attached to cutting blade 10 may enable a side-to-side sweeping motion of blade 10, which enlarges the plane of dissection. In some embodiments, tape 11 is formed of multiple strips of tape to facilitate the side-to-side sweeping motion of blade 10. Cutting blade 10 may be adjustable by the operator of endoscope 1 based on indications presented by the scalp tissue of the patient and the comfort of the operator. The operator of endoscope 1 may be able to control the amount of tissue penetration achieved by each advancement of the endoscope as well as the motion of the cutting blade 10 in the side-to-side, up-and-down, and forwards-backwards directions.

In some embodiments, cutting blade 10 may be replaced by a blunt-ended blade, an electrocautery device, a dispenser of pressurized gas or liquid, a balloon-like expanding device, an enzymatic tissue separator, a laser, or any other device capable of separating the connective tissue along a desired plane.

Referring to FIG. 6, similar to many standard endoscopes (e.g., a rigid hysteroscope), endoscope 1 has three ports. Endoscope 1 may otherwise have a different number of ports. A light port 2 allows light from a fiberoptic light cable 504 to enter endoscope 1 through proximal end 502 of the endoscope. An insufflation port 3 is the entry point for moistened insufflation gas, which facilitates, enhances, and maintains the separation of subcutaneous tissue planes. Both light received through light port 2 and insufflation gas received through insufflation port 3 pass through an outer trocar 8 of endoscope 1 and are emitted in an outer oval 6 at distal end 500 of endoscope 1. An imaging port 4 allows magnified viewing of tissue in the region of distal end 500 through a lens 5 at the beveled distal end 500 of endoscope 1. In some embodiments, an operator looks directly through imaging port 4. In other embodiments, an electronic camera is coupled between imaging port 4 and a television monitor to facilitate viewing.

Endoscope 1 may optionally include any of the features presented below, for example visualization device 1150 and extraction modules 1104, 2104.

Another example of an endoscope includes a horizontal blade that may run parallel to the surface of the skin at a known distance from a visualization probe, such as an ultrasound probe, that an operator may manipulate along the overlying skin surface.

Because cutting blade 10 is positioned directly below lens 5 and because of the beveled profile of distal end 500, blade 10 as well as the tissue through which it cuts are easily viewed.

A humidified gas such as carbon dioxide may be used for insufflation. The temperature of the gas falls between 30-33° C. The pressure of the insufflation gas ranges from 10-50 mm Hg and is determined by the scalp laxity in order to enhance the creation and maintenance of a visual cavity established by cutting blade 10. Together, the blade and insufflation pressure establish a visual cavity with a clearance of at least 1.0 mm. Such a clearance allows for the advancement of the 0.4 mm endoscope 1 and outer trocar 8 attached to cutting blade 10.

In this example, a light source 506 emitting light at a specific wavelength may allow further and deeper visualization and subsequent penetration through the scalp sub-follicular subcutaneous tissue by endoscope 1 while still retaining or improving the ability to selectively visualize hair follicle structure and essential follicle components required for self-renewal (e.g. the stem-cell containing bulb 214 and bulge 212). In some embodiments, to better view essential FU components required for self-renewal in differently-pigmented hair follicles that may be otherwise difficult to visualize, illumination light from light source 506 is filtered prior to being reflected toward the plane of hair follicles by a diatonic mirror positioned either inside or outside of endoscope 1. Exemplary fluorochrome filters include, but are not limited to: FITC (excitation wavelength=490 nm, emission wavelength=525 nm), DAPI (excitation=350 nm, emission=470 nm), or rhodamine (excitation=511 nm, emission=534 nm). When the illumination light has a range of wavelengths, light emitted from the various components of hair follicles is filtered by an appropriate emission filter positioned prior to imaging port 4.

Figure 7:
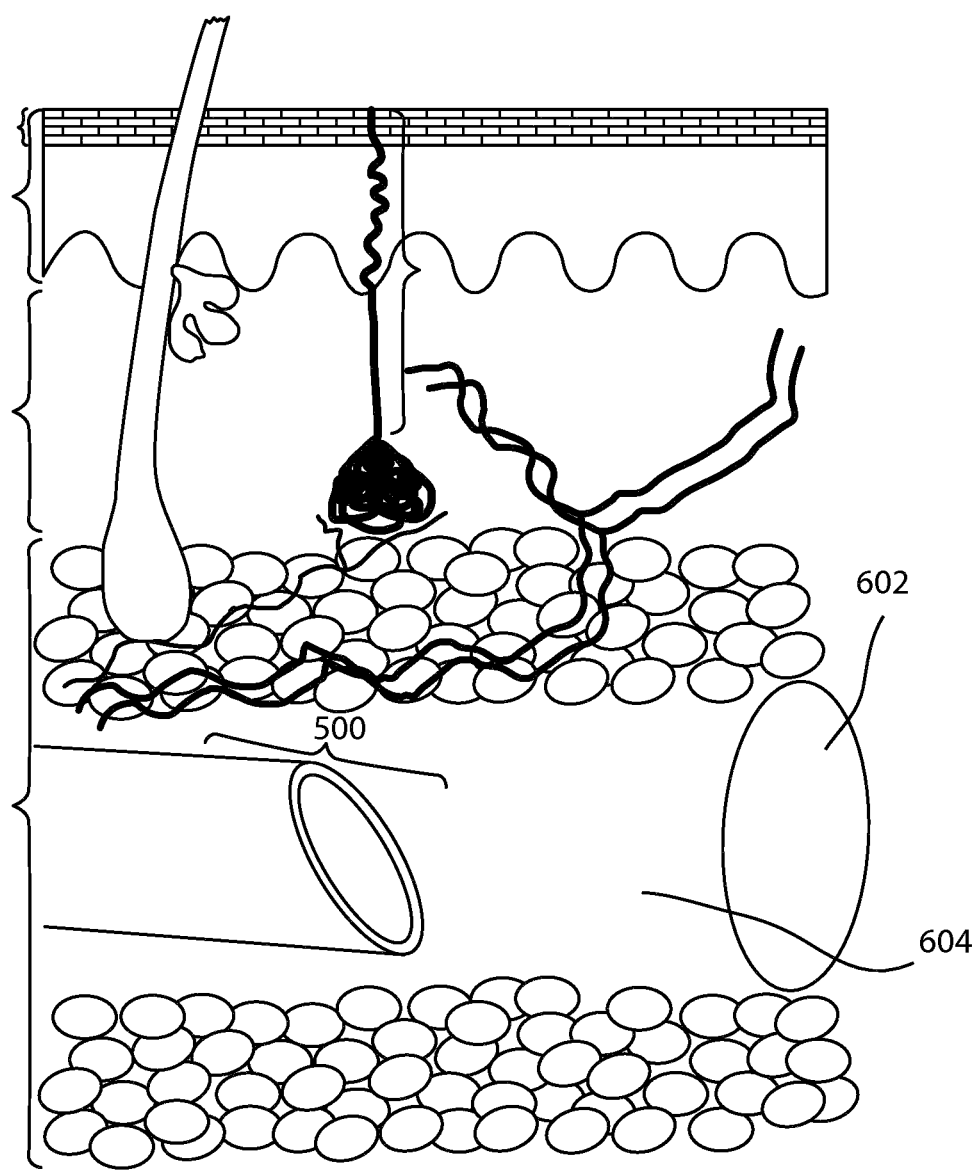
FIG. 7 is a cross section of the visual cavity created with the distal dissection blade of FIG. 6 maintained by a barrier device.
Figure 8:
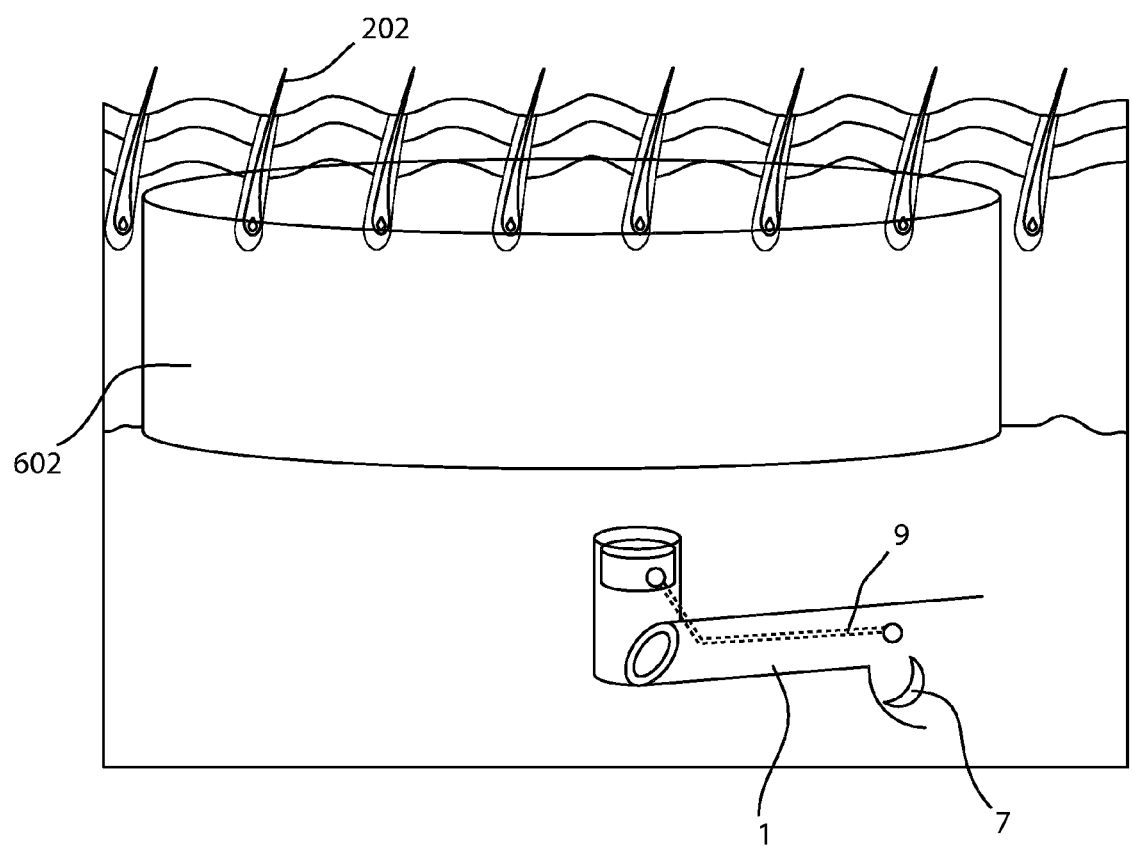
FIG. 8 is a cross section of the barrier device of FIG. 7 defining the safe donor area.

Referring to FIGS. 7 and 8, once a visual cavity 604 is established by surgical dissection using cutting blade 10, the cavity 604 is maintained by the insertion of a barrier device 602 in order to maintain ample clearance for the entrance and function of the functional portion of endoscope 500 which may carry attached tissue dissection and extraction modules. The barrier device 602 expands along the established subcutaneous plane 230 to enable the operator to define the outer border of the "safe donor zone," a region of relative donor hair follicle permanence determined pre-operatively by the surgeon on the basis of the patient's medical, surgical, and family history, the caliber and density of the patient's hair, and other physical characteristics. The safe donor zone (often seen in men as a "horseshoe rim" of permanent hair) represents a zone within which FUs will most likely continue to persist and grow throughout a patient's lifetime; outside of this zone, FUs may not be permanent. The use of barrier device 602 to surround the safe donor zone may ensure transplantation of permanent FU and prevents the inadvertent extraction of hairs outside this zone. Barrier device 602 may be actuatable by an operator to expand or turn in order to create a more voluminous cavity. Barrier device 602 may be, for instance, a balloon expander or a gripping device applying force external to the skin. In some examples, barrier device 602 may be a porous structure positioned beneath or within the skin that allows for various tissues of interest (e.g., hair follicles) to protrude through the device at desired locations in the porous structure of the device.

Expansion of the barrier device may help to facilitate identification of individual FU within a region of high hair density in the overlying skin as the inter-follicular skin surface is increased. Visual cavity 604 may be kept moist throughout the surgical procedure by periodic administration of saline spray at, for instance, 50-100 mL/hour. Humidified insufflation through insufflation port 3 is preferably performed at least about every 5 minutes.

Figure 9:
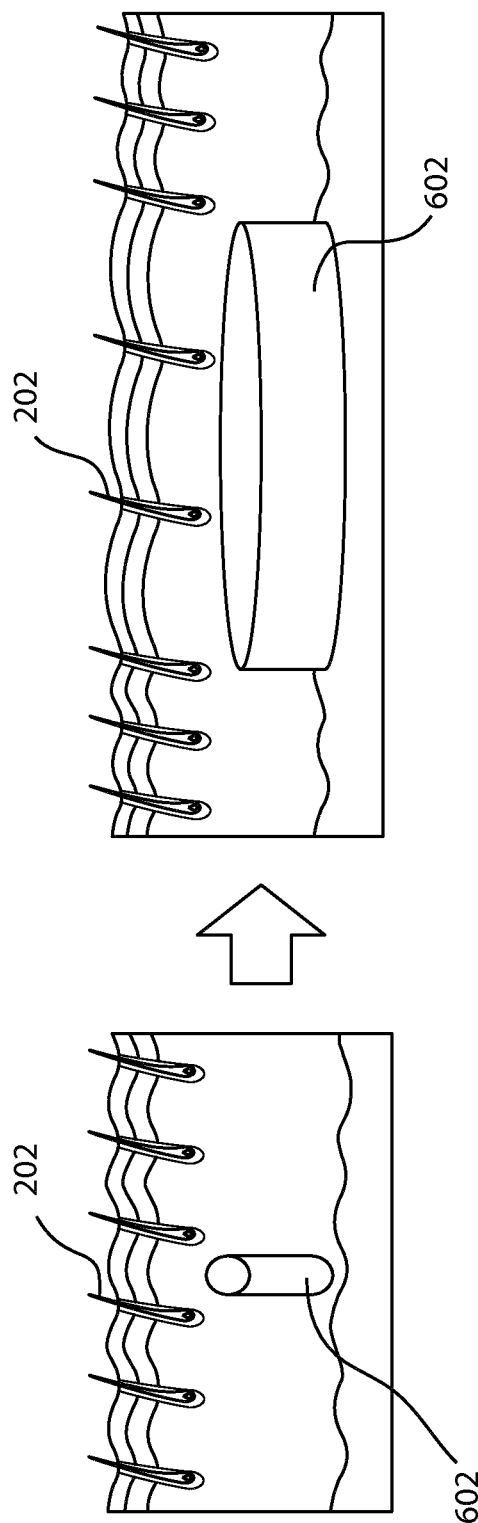
FIG. 9 is a cross section view depicting how the barrier device of FIG. 8 increases the distance between each hair follicle.

Referring to FIG. 9, the barrier device 602 may also be used to expand the surface area of the intact skin above, increasing the distance between adjacent hair follicles 202 (or, in other applications, increasing the distance between each relevant tissue region of interest). The spreading of the skin does not injure the hair follicles or the skin, but rather temporarily increases the natural spacing between adjacent follicles. This spreading facilitates visualization, identification, and classification of the hair follicles from beneath the surface of the skin. The barrier device 602 creates and retains an enlarged visual cavity beneath the surface of the skin while it is in place; once the device is removed, the overlying skin surface area is reduced to its original state.

Figure 10:
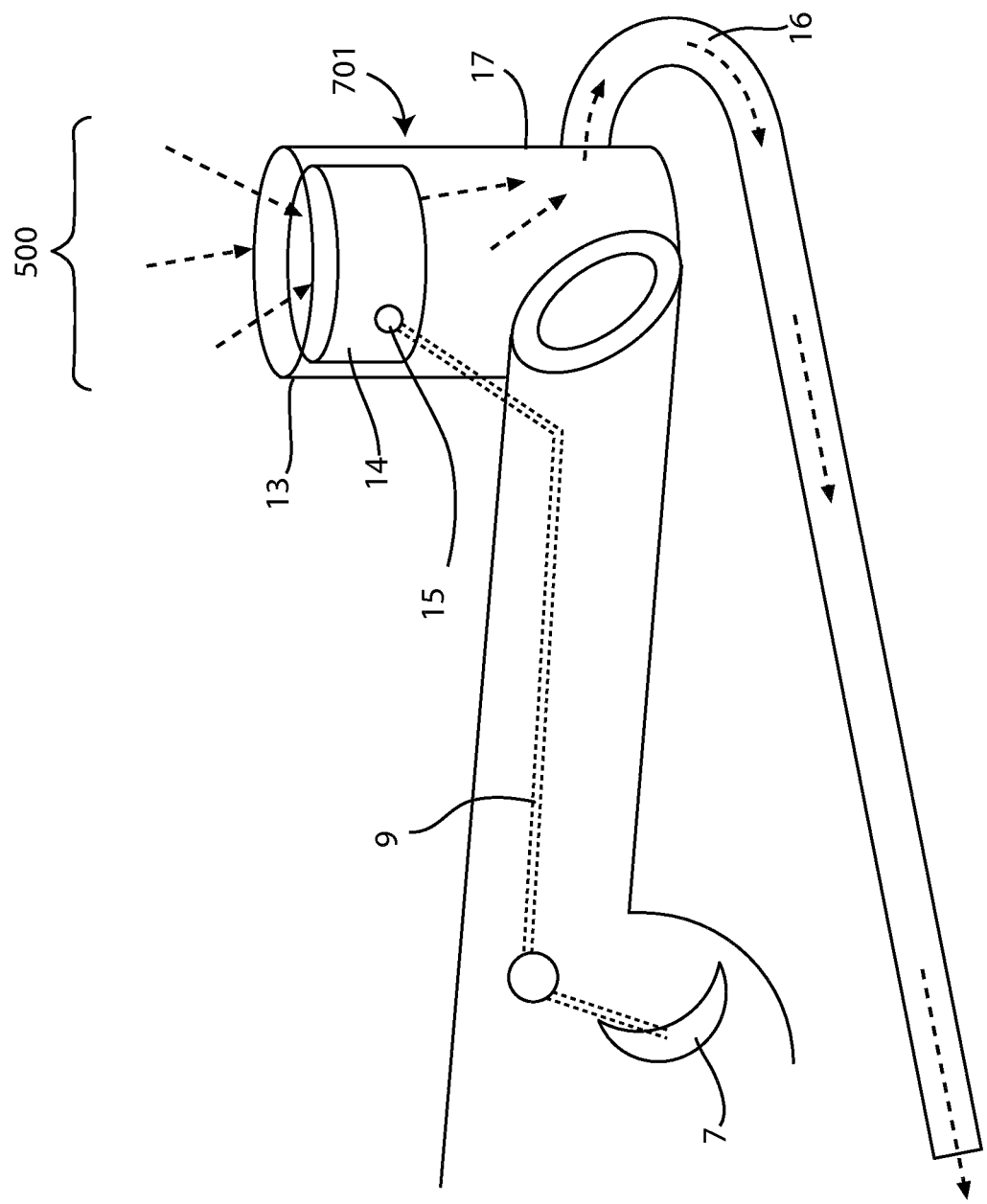
FIG. 10 is a side view of an endoscope with an extraction device attachment.
Figure 11:
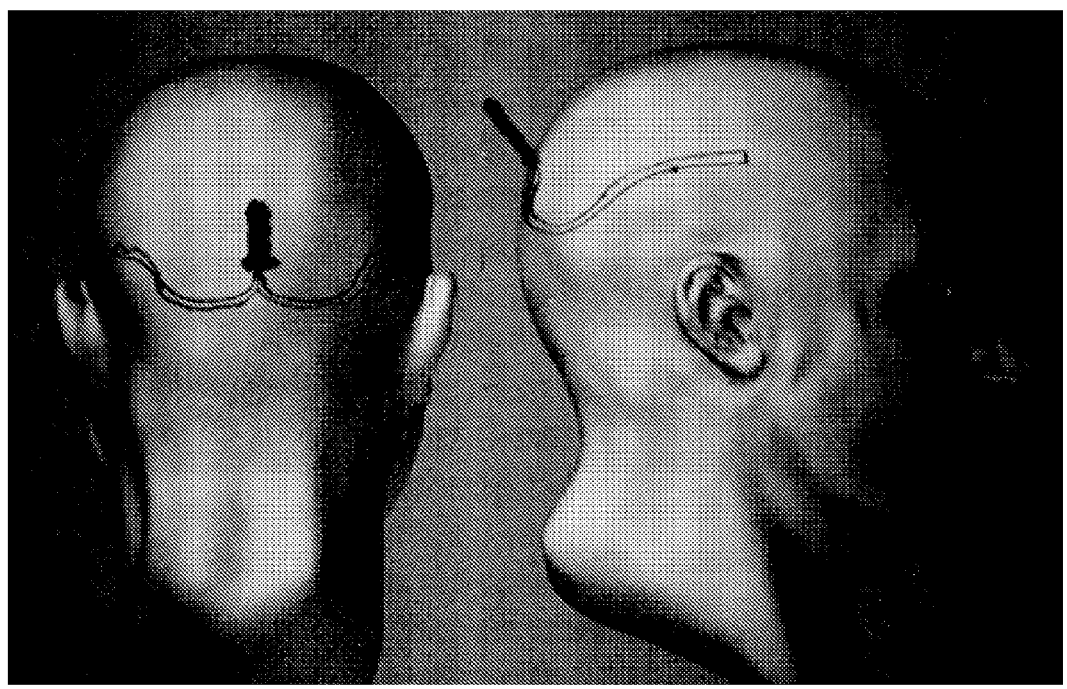
FIG. 11 is a front and side view of a human head with a track system implanted.
Figure 12:
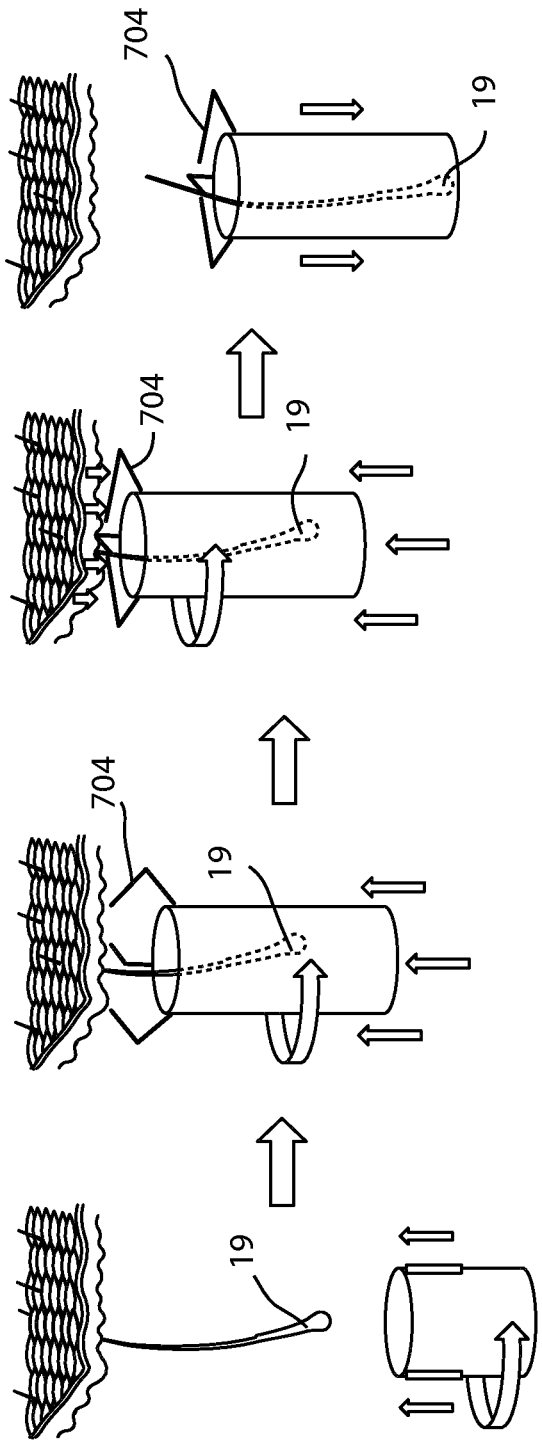
FIGS. 12A-12D are side views of an extraction module during the process of follicular unit extraction.

Referring to FIG. 10, once surgical dissection of the visual cavity is completed and a clearance of at least 1.0 mm is maintained to ensure safe passage of surgical instrumentation, an extraction device 701 is attached to distal end 500 of endoscope 1 and used to isolate, punch, and remove intact hair follicles. A track device, such as the one illustrated in FIG. 11, may also be used to facilitate subsequent hair follicle harvesting by providing a track or guide or scaffold on which a coring or clipping device may ride towards the safe donor zone and the follicular units that have been identified as desirable for transplantation.

In the embodiment depicted in FIG. 10, extraction device 701 is a cylindrical punch-type component. However, in other embodiments, the extraction device may be an oval, cuboid, or hooked device, or another device having curved or straight edges and capable of performing the relevant functions. Extraction device 701, which may also be referred to as an extraction module or extraction component, may contain two concentric cylindrical components: a coring cylinder 20, which may also be referred to as a coring cannula, used to pierce the adipose and dermal tissue surrounding the bulb of an intact hair follicle 19, and a clipping cylinder 14 or clipping cannula. The coring cannula 20 may include a beveled-edged portion. The clipping cannula may possess a series of inward angled levers 704, as illustrated in FIGS. 12A-12D, that act to cut the final epidermal tissue to which the intact follicle remains tethered in order to isolate the follicle from surrounding tissue. In other embodiments, coring cylinder 20 may be blunt-edged and may press against the sub-follicular, subcutaneous tissue from below to stabilize the device so that the coring cylinder 20 can engage the tissue prior to coring. The clipping cylinder 14 may be driven by a lever 15 that can be controlled by the operator via a cable 9 attached to a trigger 7 at the proximal end of the endoscope 1, as seen in FIG. 10. A central axis of the extraction device 701 that extends through the coring 20 and clipping 14 cannulas may be generally oriented at an angle to the longitudinal axis of endoscope 1 in order to facilitate flow through the extraction device along a defined removal pathway.

Although the extraction device described herein is composed of two concentric components, in other embodiments, extraction device 701 may be a single entity.

An operator of endoscope 1 views a follicle 19 in its entirety through visual lens 5, as seen in FIG. 6, from within coring cylinder 20. The operator is thus constantly aware that all components important for follicular self-renewal are included in the dissection process.

Figure 13:
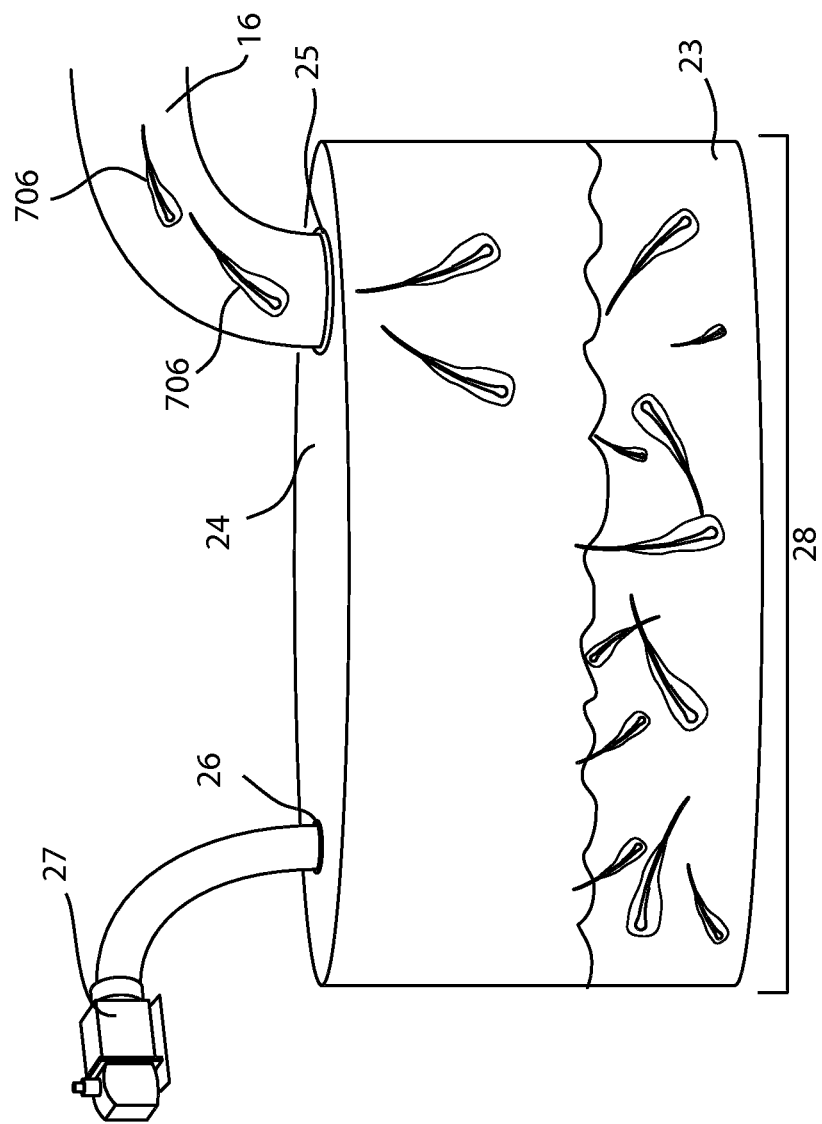
FIG. 13 is a side view of a graft preservation tank.

As illustrated in FIG. 13, extraction device 701 may be connected to a moistened vacuum suction tubing 16 that defines at least a portion of the removal pathway, which is in turn connected to a vacuum source 27. The vacuum source provides suction that flows from above extraction device 701 downward toward vacuum tubing 16. The vacuum effect is readily activated/deactivated and/or increased/decreased by a switch, button, voice control or foot pedal attached to vacuum source 27.

In some examples, an extraction device and a cutting blade, which may share characteristics with cutting blade 10, may be affixed together onto a single portion of an endoscope. Referring to FIGS. 14-18, another example endoscope is illustrated. Surgical instrument 1100 includes an extraction device and a cutting blade that are affixed to a distal arm of an instrument that allows for mirrored or synchronized movement of a visualization component and an extraction component. Surgical instrument 1100, which may be referred to as a C-arm device, may be an endoscope, and may share some of the characteristics and functionality of the endoscope 1 described above. The C-Arm device is described for removal of a target region of tissue, which includes a hair follicle. The system may be adapted for body hair removal, or removal of hair from a scalp. Surgical instrument 1100 includes a "C-shaped" member 1102, which may also be referred to as a C-arm, an extraction module or extraction component 1104, and an external reference module 1106, which may also be referred to as a visualization module or external guidance module.

The C-arm may be rigid or flexible, and may include a proximal first arm 1108 and a distal second arm 1110 that extend from a middle portion 1112, which may also be referred to as a bridging component. The bridging component 1112 may serve to physically couple the external reference module, which may be carried by the first proximal arm 1108, and the extraction module, which may be carried on the second distal arm 1110. The first and second arms 1108, 1110 may extend substantially perpendicular to the middle portion 1112, or at least generally parallel to each other. The middle portion 1112 may be congruent and integral with a proximal handle portion 1114. The middle portion 1112 and proximal handle portion 1114 may be aligned along an axis 1140. The first arm 1108 may include a guide portion 1118, and may be coupled to a visualization or external reference device. The second arm 1110 may carry a tissue extraction module 1104 with a coring cannula and a clipping cylinder, similar to extraction device 701. The second arm may also carry a dissection blade (not illustrated), which may be similar to blade 10, which may be used to help create a visualization cavity.

The proximal first arm 1108 may be slidably attached to the instrument 1100, or may be fixed to the instrument 1100. The proximal first arm 1108 may include a flat portion 1116 and a curved guide portion 1118. The flat portion 1116 may extend between the middle portion 1112 and the guide portion 1118. The guide portion may include an elongated slot 1117 that carries a portion of a visualization module 1106.

The second distal arm 1110 may include a base component 1120 and a platform 1122. The platform 1122 may also be referred to as a tissue guard or a tissue shielding device.

The platform 1122 may include at least one aperture 1124 and a first beveled end portion 1126. The base component 1120 may have a hollow interior and a second beveled end portion 1128.

The length and shape of the second distal arm 1110 may vary. For example, the second distal arm 1110 may be contoured to match the contour of a portion of a human skull. The second distal arm 1110 may have a concave skull facing surface when the instrument 1100 is held in a working orientation with regard to the skull. The degree of curvature of the second distal arm 1110 may be fixed, or the distal arm 1110 may be flexible in order to allow the curvature to adjust in response to the curvature of the skull when the instrument 1100 is moved along the skull. The second distal arm 1110 may otherwise be straight and/or rigid.

The extraction module 1104 may be removably attached, and at least partially contained within the base 1120 of the distal second arm 1110 of the C-arm 1102. At least a portion of the extraction module 1104 may be movable relative to the second arm 1110 toward the external reference module 1106. The extraction module 1104 may include a suction port and a tissue removal implement 1138, which may also be referred to as a tissue removal component.

Figure 20:
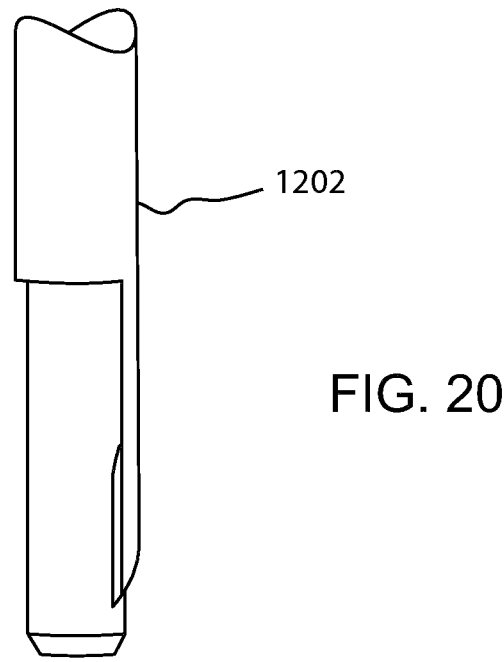
FIG. 20 is a side view of another coring and clipping module.
Figure 21:
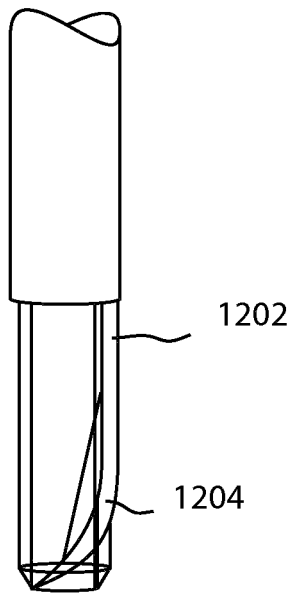
FIG. 21 is a side view of yet another coring and clipping module.
Figure 22:
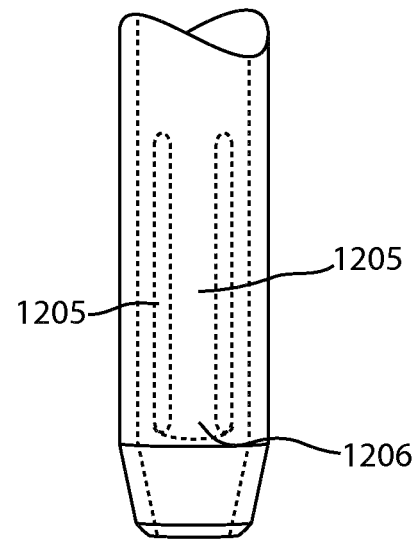
FIG. 22 is a side view of yet another coring and clipping module.

The tissue removal implement, which may be referred to as tissue removal component 1138 (FIGS. 36-38) may include a cannulated system, similar to extraction device 701 designed to core and clip a target follicular unit from an internal tissue surface. Referring to FIGS. 19-22, various examples of a tissue removal tip 1200 are illustrated. The tissue removal tip, which may also be referred to as a coring device 1200, may include an outer shaft 1202, which may be referred to as a clipping cannula. The clipping cannula 1202 may include one or more clipping elements located at a superficial border of the tissue removal component. The clipping elements may be described as blades, although other cutting features, such as teeth, are contemplated. There may be a plurality of cutting devices, such as curved blades, teeth, or other cutting features that are disposed around the superficial border of the tissue removal component 1138. In the device shown in FIG. 19, the tip 1200 includes two blades 1204 that interact with an internal coring cannula 1206. When the two blades 1204 interact with the coring cannula, the blades 1204 may be urged towards one another, similar to the mechanism of a traditional fingernail clipper. Illustrated in FIGS. 20-22, alternative examples of the clipping cannula are illustrated. Referring to FIG. 20 the tip 1200 may alternatively have a single blade that is urged inwards to clip a hair follicle. Alternatively, the tip 1200 may include a plurality of prongs 1205, like those illustrated in FIG. 22. The prongs may be activated to deploy internally into the coring cannula 1206 and clip a target tissue from the surrounding tissue for removal.

In use, the coring cylinder 1206 may be manipulated to engage subcutaneous adipose tissue 700 deep to hair follicle 19 using a combination of 1) operator-driven movement upwards controlled at the proximal end of the endoscope, and 2) vacuum suction downwards generated from vacuum tubing 16. The combination of upwards and downwards force may act to create a tight seal 15 between extraction device 701 and peri-follicular subcutaneous soft tissue 700, thus stabilizing the tissue with respect to endoscope 1100 and ensuring proper isolation and subsequent controlled removal of intact hair follicle 19. This can be seen best in FIGS. 23A-23D. The tissue removal component 1138 may be actuated to core and clip a desired tissue section through a trigger mechanism that translates the motion of the trigger to a rotational motion of the tissue removal component 1138. For example, once a suction seal has been established, the operator may press or pull on a trigger 7 to engage a lever or other motion translation system to advance the tissue removal 1138 component from a first position to a second position while still attached to the base of coring cylinder 1206 thus moving the coring cylinder 1206 upwards in a twisting fashion. The coring cylinder 1206 may be twisted either clockwise or counterclockwise as it is moved upwards, and the direction of rotation may be reversed when the extraction device later pulls downwards.

The instrument 1100 may be coupled to a motor unit 1101 that is removably connected to the instrument. The motor unit 1101 may be snapped or otherwise fitted into a groove that extends along the length of the intermediate portion 1112 and the proximal handle 1114.

Manipulation of the coring cannula may be performed through an arrangement of gears that transforms rotation of an output shaft of the motor unit 1101 to rotation of the coring cannula 1206 as illustrated in FIGS. 24-30. More specifically, a pair of 45 degree bevel gears 1212, 1214 may be used to change the direction of rotation by 90 degrees where the second arm joins the intermediate portion 1112. Motor shaft rotation about axis 1140 is transformed into drive shaft rotation about an axis 1218 along the second arm 1120. A first one of the bevel gears 1212 is secured to the motor output shaft 1216 and the second bevel gear 1214 is secured to a first end of a drive shaft 1220 that extends along the second arm. The opposite end of the drive shaft terminates in a third bevel gear 1222 which engages a fourth bevel gear 1224 (or crown gear). The third and fourth bevel gears 1222, 1224 interact to change the direction of rotation by another 90 degrees so that the fourth bevel gear 1224 rotates about an axis 1226 which is perpendicular to both the motor output shaft axis 1140 and the drive shaft axis 1218. The fourth bevel gear 1224 interacts with a fifth bevel gear 1228 to change the direction of rotation by another 90 degrees so that the fifth bevel gear 1228 rotates about an axis 1230 which is perpendicular to the axis 1226 of the fourth bevel gear 1224, and lies in the same plane as the motor output shaft axis and the drive shaft axis 1218. The fifth bevel gear 1228 is coupled to the coring cannula 1206, and thus rotation is transferred through this arrangement of gears from the motor 1101 to the coring cannula 1206.

This arrangement makes it possible to vary the angle between the drive shaft axis and the axis of the fifth bevel gear in order to align the extraction module 1104 with a preferred orientation of a target tissue, such as a hair shaft in a follicle, and then rotate the coring cannula 1206 during the extraction process. One arrangement to control and manipulate the extraction module makes use of a linkage which allows the fifth bevel gear 1228 to pivot about the fourth bevel gear axis. The linkage includes a rocker bar 1232 (FIG. 28) which carries the fifth bevel gear 1228 at one end, connects to a first bar 1234 at the other end, and is hinged 1236 in the middle to the fourth bevel gear 1224. The first bar 1234 extends alongside the drive shaft 1220, and hingedly connects within the middle portion 1112 to a second bar 1238. The second bar 1238, which may be rather short, extends generally along the motor output shaft axis 1140 to connect to a third bar 1240. The third bar 1240 may extend much farther up the handle, and may also extend generally along the motor output shaft axis 1140. The second and third bars 1238, 1240 may also be integrally formed with one another. The third bar 1238 may connect to a control button (not shown) slidably or depressably mounted to an exterior handle housing (also not shown).

Figure 28:
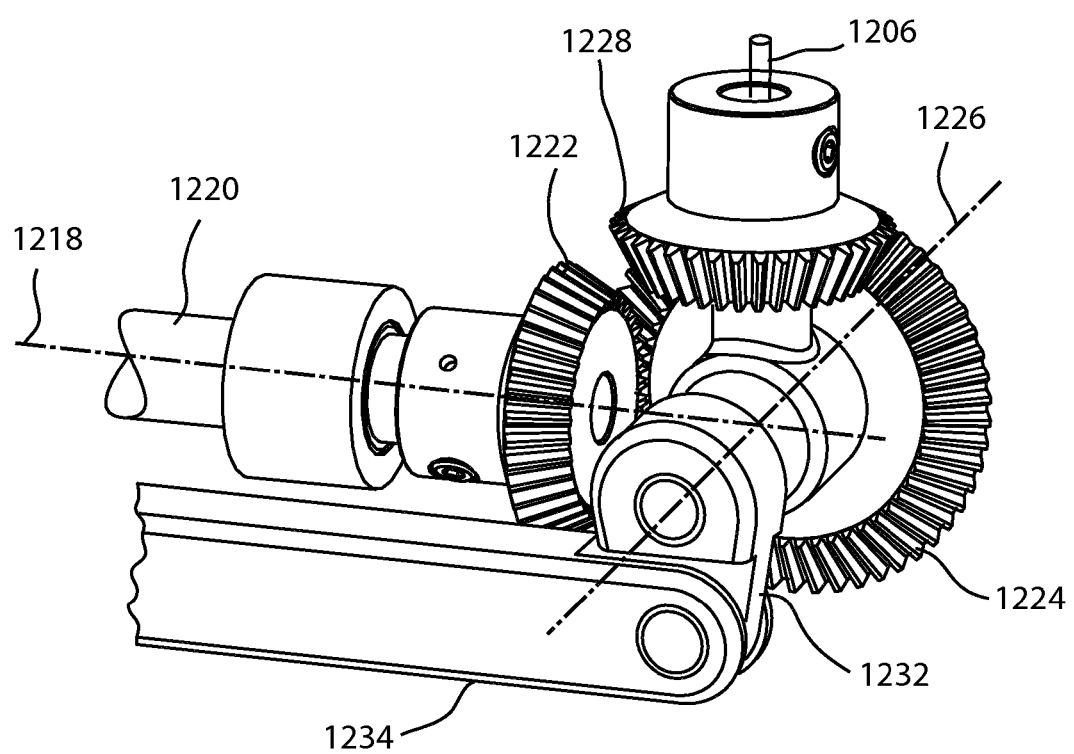
FIG. 28 is a top perspective detail view of the beveled gear assembly of FIG. 27.
Figure 29:
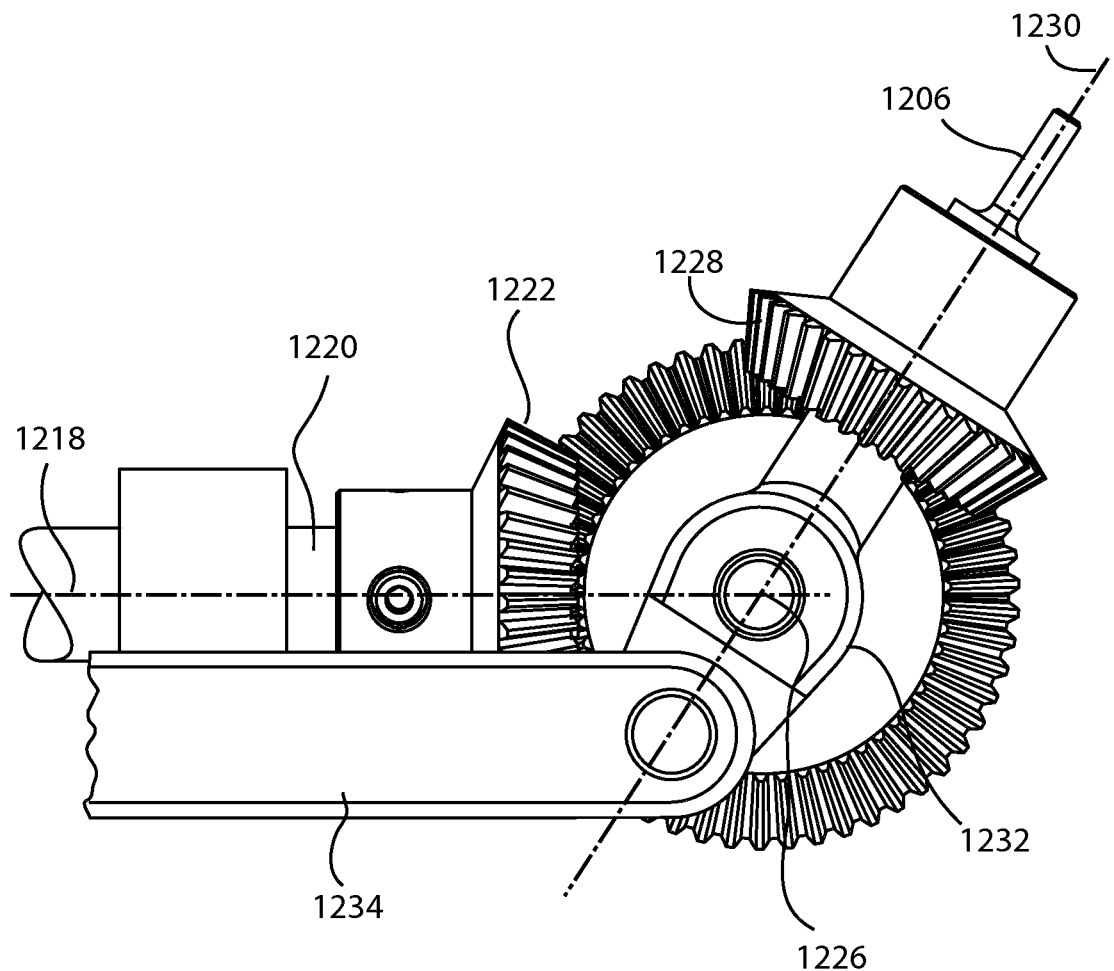
FIG. 29 is a side detail view of the beveled gear assembly of FIG. 27 in a second position.
Figure 30:
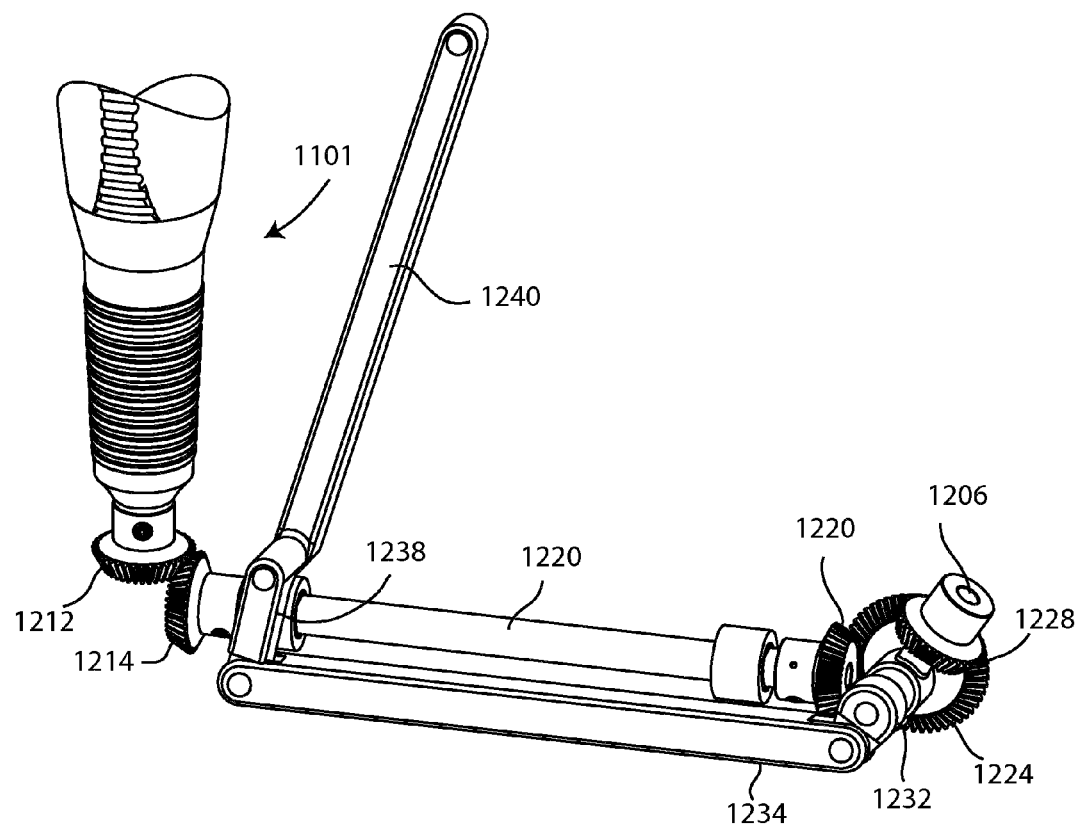
FIG. 30 is a top perspective view of the gear assembly of FIG. 24.
Figure 31:
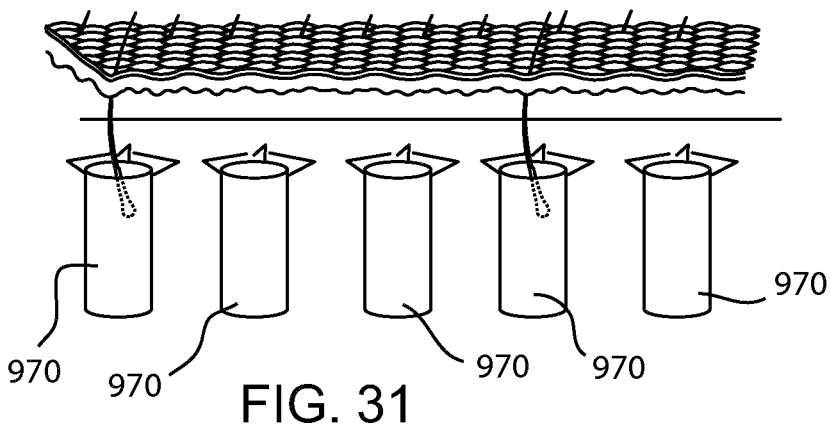
FIG. 31 is a side view of multiple cylindrical punches.
Figure 32:
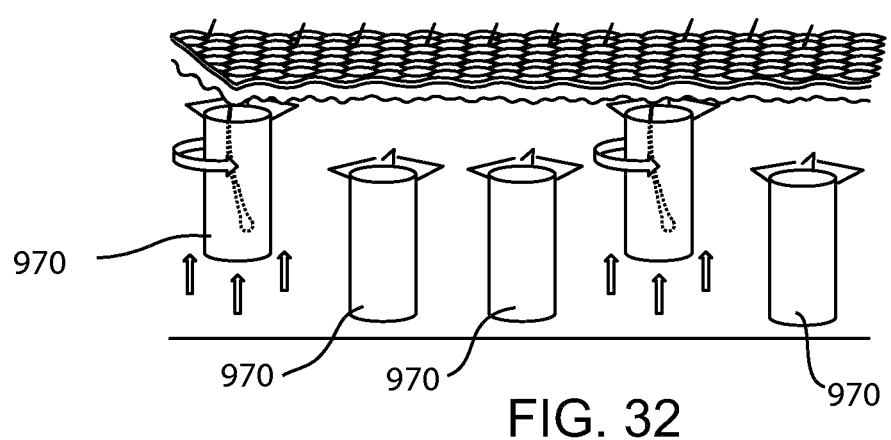
FIG. 32 is a side view of multiple cylindrical punches, some of the punches engaging hair follicles for removal.
Figure 33:
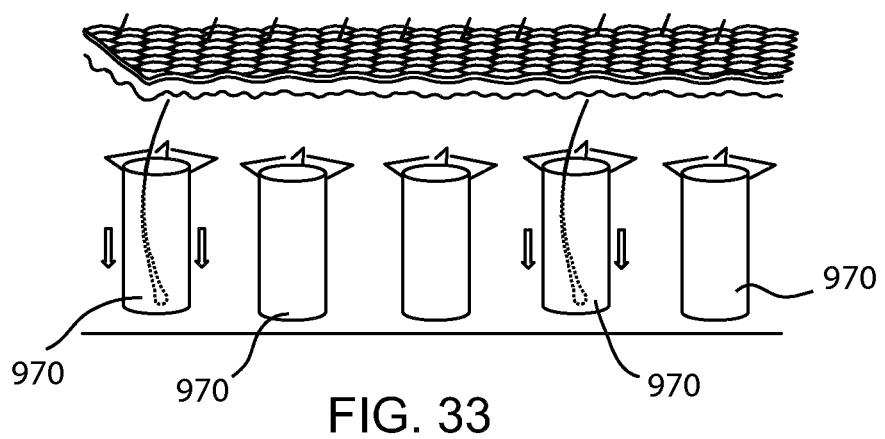
FIG. 33 is a side view of multiple cylindrical punches after removal of hair follicles from the surrounding tissue.

The rocker bar 1232 may be integral with the assembly, or may be a subassembly or components in a fixed mutual relationship (FIG. 28).

One of skill in the art will recognize that the various bevel gears, shafts, and bars may be assembled with dowel pins, bolts, screws, nuts, and the like. Various bushings and supports may also be included in this apparatus in order to maintain the various components in their desired positions and relative orientations. For example, the second bevel gear may be constrained to mesh with the first bevel gear by a bushing or bearing that permits the drive shaft to rotate, but holds the second bevel gear in intimate contact with the first bevel gear. Similar arrangements may be employed for the third and fourth bevel gears, so that the first through fourth bevel gears are in fixed orientation. The fifth bevel gear, which is mounted to the rocker bar, is pivotally movable relative to the arrangement of first through fourth bevel gears. The rocker bar, however, is hinged in its middle to the fourth bevel gear so that the rocker bar rotates about the fourth bevel gear axis. Additional support, in the form of fixed, sliding, or pivoting connections, may be provided along the remaining bars of the linkage.

The tissue removal component 1138 may also include a detection device or stop mechanism that prevents the coring cylinder from piercing the stratum corneum or from cutting tissue within a predetermined distance from the skin surface (e.g. less than 1 mm, or about 0.74 mm, which is the depth below the surface at which the stem cell-containing isthmus begins). The stop mechanism (not shown) may include a mechanical bumper that prevents the coring device from piercing more than a predetermined distance from the skin surface.

The stop mechanism may further be enabled by an innate feedback mechanism based on a gradient of resistance within the skin. For instance, if the coring cylinder is cutting using rotational torque, the rotational frequency is lessened as the coring cylinder moves closer to the skin surface because of the increased resistance posed by the increased collagen and fibrin content in the epidermis and the stratum corneum (i.e., following the equation $V=IR$). In some cases, an operator can detect the desired proximity of the cutting device to the stratum corneum via feedback from the detection device and can stop the cutting based on this feedback. The detection device therefore may act to ensure that no trauma is inflicted to the stratum corneum, and to avoid disruption of the structural integrity of the intact hair follicle as it is isolated and removed.

The instrument may also include a mechanism for more accurately aligning a hair follicle with an extraction axis prior to follicular extraction. The instrument may include a dermal shifter (not shown) that provides a uniform manipulation of the dermal tissue surrounding a hair follicle. The dermal shifter may include a series of small needles at a known distance from a hair follicle of interest beneath the skin surface. A dermal shifter may also be used on an exterior skin surface.

For example, the dermal shifter may include four 30-gauge needles arranged in a box-like orientation around a target follicle. Once the needles have been placed around the target follicle, the needles may be actuated to shift the desired follicle into a more desirable alignment for subsequent extraction. This uniform manipulation may enable the transition of a hair follicle that exists at an acute angle with respect to the skin surface to a more perpendicular angle during extraction. The alignment of the hair follicle in a perpendicular fashion beneath the skin surface may facilitate the subsequent coring and clipping of the follicle from beneath the skin surface without disrupting the integrity of the overlying skin surface.

Once the coring cylinder 1206 has been positioned at the desired predetermined depth from the skin surface and has been sufficiently aligned with the hair follicle to be removed, the coring cannula 1206 with the associated clipping cannula 1202 with cutting devices, such as multiple inwardly-curved blades, may be rotationally or vertically manipulated to move towards the center of the coring cylinder 1206 in which the hair shaft lies, as previously described.

In some embodiments, clipping cylinder 1206 may be composed of semi-flexible metal (e.g., nitinol) enabling the clipping devices to lie flush along the surface of the coring cylinder 1206 when retracted and to resume their inward-angled position once the clipping cylinder 1202 is advanced beyond the distal tip of the coring cylinder 1206. The downward force from the intact stratum corneum above may also help direct the inward-angled levers further inward, increasing their ability to clip the remaining epidermal tissue.

The shearing of the superficial layer of epidermis 1204 by these cutting devices may reach the hair shaft to separate the follicle from its native tissue. The vacuum force may draw the separated follicle downwards into the moistened tubing 16 and along the removal pathway.

The tissue removal component 1138 may also include one or more gripping ledges or keels disposed on the inner surface to facilitate enhanced tissue removal. For example, once the upper, superficial border of the to-be-isolated hair follicle 19 has been sufficiently separated by the cutting devices, the operator may activate trigger 7 to cause coring cylinder 1206 to be pulled downward in a twisting fashion, rotating in the opposite direction from its rotation upon upward movement. Microscopic, one-way, gripping ledges (akin to hooks) protruding from within coring cylinder 1206 may grasp the peri-follicular tissue 1208, 1206, and 1204 that surrounds hair follicle 19 as coring cylinder 1206 is pulled downward, rotating in the opposite direction from its rotation upon upward movement. The gripping and tugging motion of the microscopic ledges within the cylinder may be coupled with curved blades 704 that rest atop, or superficial to, the soon-to-be isolated hair follicle 19 to provide mechanical pressure to pull the follicle 19 out of its native, soft-tissue environment.

Although the cutting devices 704 are described above as sharp blades, other variations are also possible, including a rotational blade or lever, a laser, an enzymatic solution, fluid jet, or another type of cutting device appropriate to the surgical situation.

Once follicle 19 separates from its native tissue, clipping cylinder 1102 may be reset, for example by the release of a trigger 7. In an alternative embodiment, an endoscope may include an extraction module in which the coring and clipping components remain stationary, or may rotate without vertical motion. In this example, endoscope 1100 may include a tissue manipulation component (not shown) that acts to urge the tissue towards and into the cannulated portion of the extraction module. Once the tissue has been urged into contact with the cannulated portion of the extraction module, the extraction module may be actuated by a lever, trigger or other device to core and clip the tissue.

Figure 14:
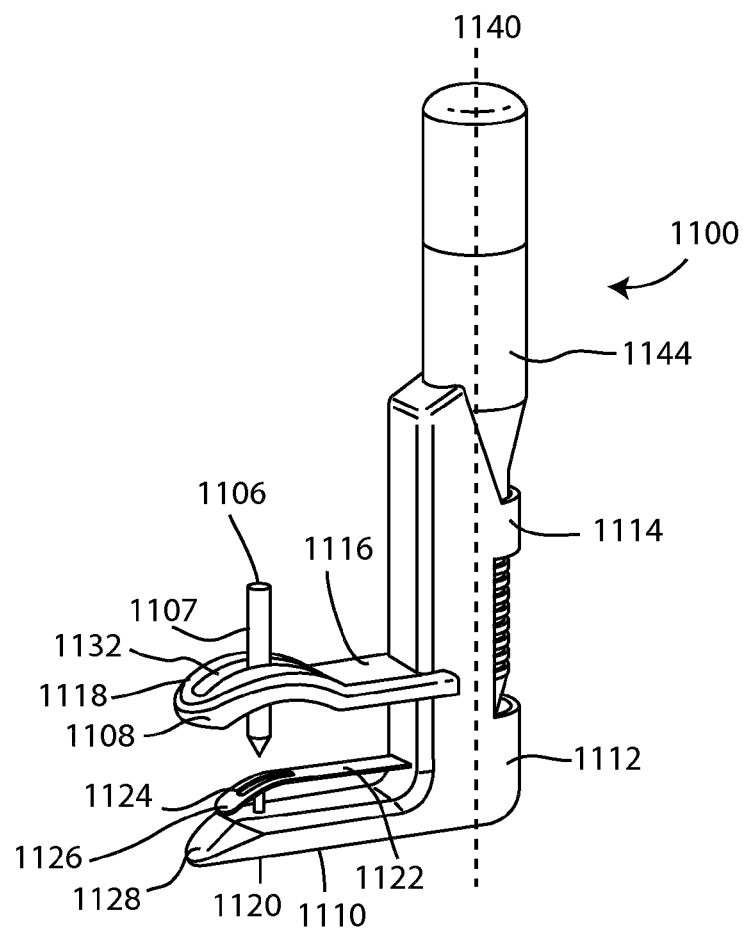
FIG. 14 is a perspective view of another endoscope instrument for follicular unit extraction with a visualization module.
Figure 15:
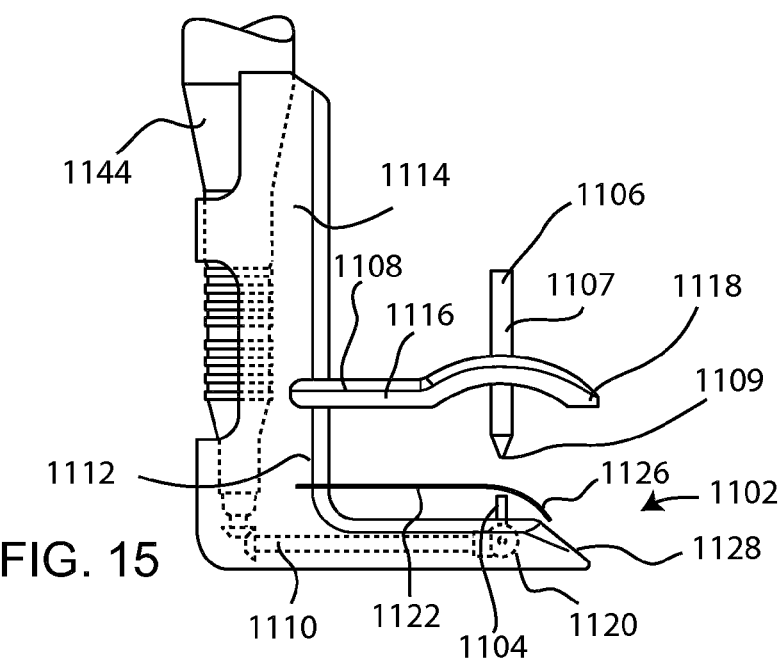
FIG. 15 is a side view of the instrument of FIG. 14.

As seen best in FIGS. 14 and 15, the tissue removal component 1104 may extend perpendicular to the base 1120 and may be aligned with the aperture 1124 of the tissue guard or platform 1122 of the distal second arm 1110. Tissue guard 1122 may act to effectively shield the environment around the desired tissue of interest from any undesired trauma (e.g., mechanical, chemical, laser-induced, or electrical trauma). Because the tissue guard 1122 may be associated closely along the coring cylinder 1206, no tissue is able to fall between the protective device and the coring cylinder 1206. Therefore, all tissue not within the coring cylinder 1206 (i.e., not the tissue of interest or the native environment surrounding the tissue of interest) will be protected by the shielding device from any subsequent activity (e.g., clipping, shearing, etc.) that takes place within the tissue guard 1122. Once the guard 1122 is held in place close to the skin surface and snugly around the coring cylinder 1206, the clipping device 1200 is engaged within it in order to isolate the tissue of interest. Alternatively, the guard 1122 may be attached to the distal end of the coring cylinder 1206 and remain around the tissue of interest as the coring cylinder 1206 is replaced by the clipping cylinder 1202. Alternatively, the guard 1122 may ride as a cylinder snugly along the coring cylinder 1206 and expand into a cone once it reaches the tissue surrounding the tissue of interest (not shown). Alternatively, the guard 1122 may be in the form of a conical or cylindrical "cage" that is separate from the first arm, and surrounds the clipping device to prevent the surrounding tissue from any trauma that could otherwise be caused by movement of the clipping device during tissue extraction. The guard 1122 may be formed of metal, plastic, rubber, or any biologically safe material.

In addition to providing a protective barrier around the desired tissue of interest, the guard 1122 may also assist in the subsequent step of isolating the desired tissue of interest. For instance, if the guard 1122 and the isolation technique are mechanical, the guard 1122 may provide guidance for the path and curvature of the isolation device (e.g., mechanically reshaping or re-aligning a "clipping" device as it presses against the inner walls of the guard 1122). Alternatively, the guard 1122 may assist in a laser-based extraction of the desired tissue by redirecting the cutting lasers inwards near the surface of the skin based on the inward sloping of the inner walls of the guard 1122.

In general, when using the tissue shielding device, after the visual cavity is established, the tissue coring device identifies and aligns with the tissue of interest, and the coring device cores around the intact tissue of interest, as described above. The guard is then engaged to isolate the native tissue environment from the tissue of interest. If expandable, the guard is deployed to assume its optimal shielding (e.g., conical) shape. Once the guard is engaged, the coring device is withdrawn. The clipping device is engaged within the established barrier of the guard. The clipping device isolates (i.e., "clips") the desired tissue of interest and then is withdrawn. Finally, the guard is withdrawn.

In yet another alternative embodiment, the endoscope may include multiple tissue extraction modules. Referring to FIGS. 31-34, an alternative piloscope may feature multiple tissue extraction devices 970 capable of harvesting separate segments of tissue simultaneously. In one embodiment, the multiple tissue extraction devices are connected by a bridging component. In another embodiment, a single extraction device has an elongated distal end that encompasses multiple tissue segments to be harvested. As described above, the desired tissue may be analyzed with a visualization device that is calibrated to correspond with the position of the extraction device(s). The operator of the device selects the individual segments of tissue to extract based on the information provided by the visualization device. Once selected, those desired segments of tissue are engaged and extracted by the corresponding tissue extraction devices, but not by those devices that were not selected and activated.

Figure 34:
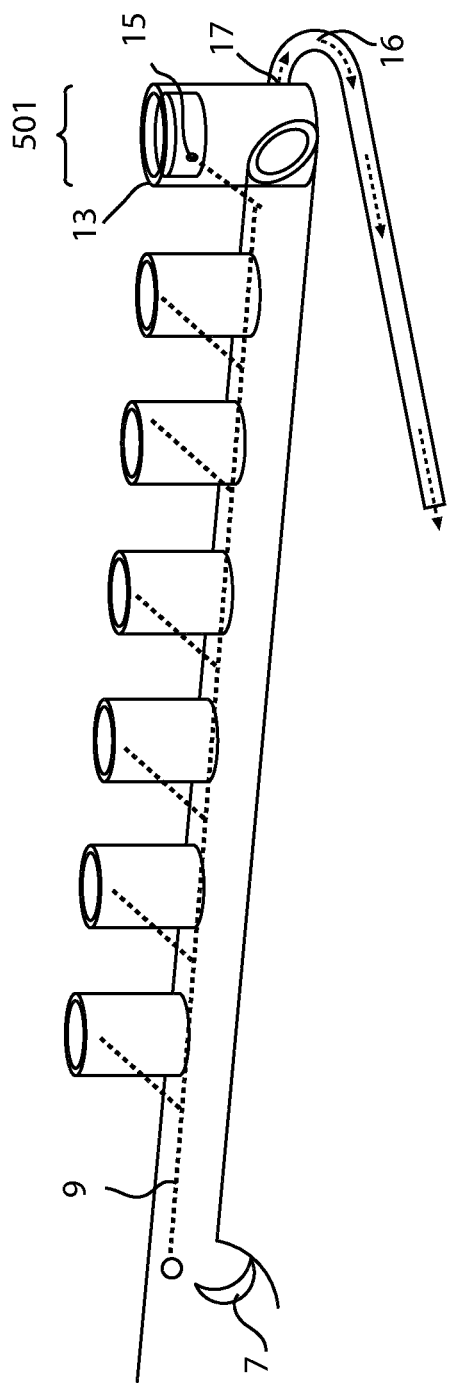
FIG. 34 is a top perspective view of multiple cylindrical punches connected to an endoscope and a removal pathway.
Figure 35A:
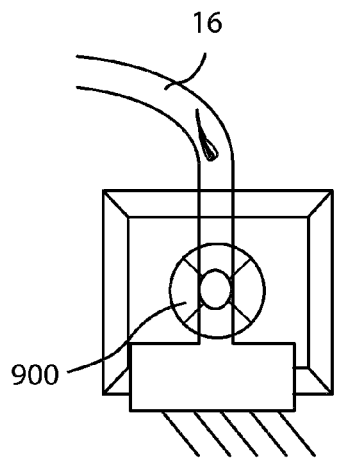
FIGS. 35A-35D are side views of a tissue identification and separation unit with a sensor.
Figure 35B:
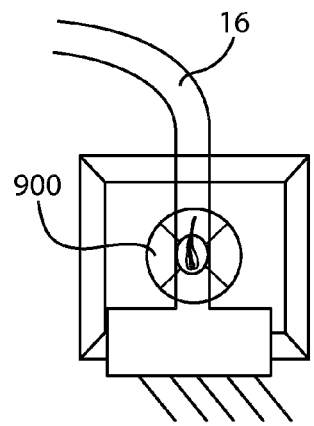
Figure 35C:
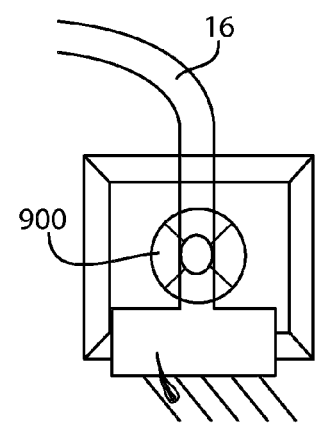
Figure 35D:
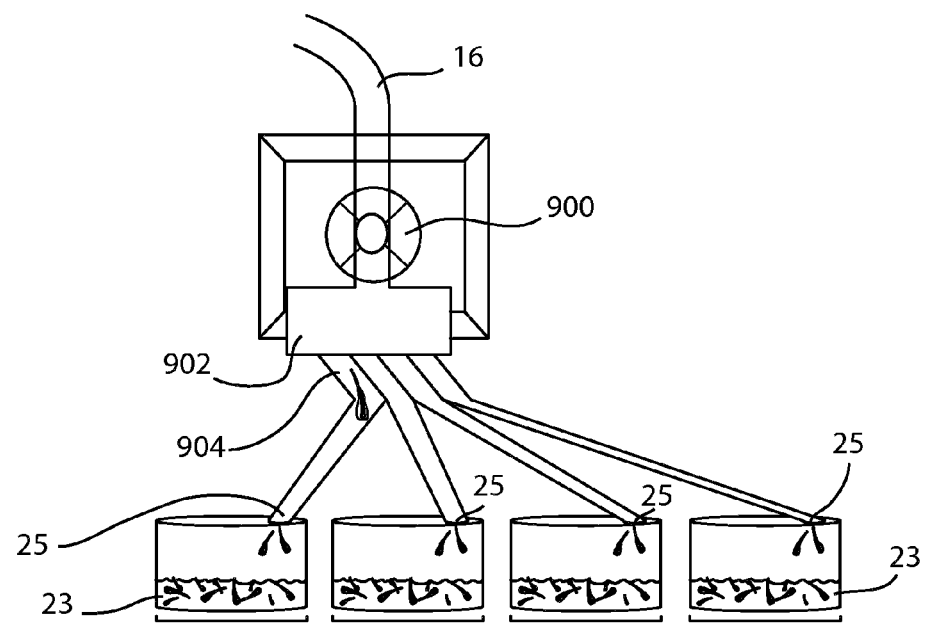

In one example, ten separate cylindrical punch devices, each attached to a singular suction portal through which the extracted tissue travels, are connected via a linear rod. The multiple punches within the internal visualization cavity (beneath the skin surface) can be controlled either mechanically, as illustrated in FIG. 34 or electronically by the operator of the device from outside of the body. A corresponding visualization device, such as an ultrasound, may be used externally or within the same plane of tissue to identify which of the ten separate cylindrical punch devices corresponds to an overlying hair follicle. The operator then activates only those punches that are aligned with the desired follicles. Each of those punches can be activated simultaneously to extract the four identified follicles, leaving the remaining undesired tissue intact. All four of the follicles are extracted and travel through the same vacuum port to a common storage vial. The multiple-extractor device is then moved to a new region of tissue to begin another extraction.

Figure 23A:
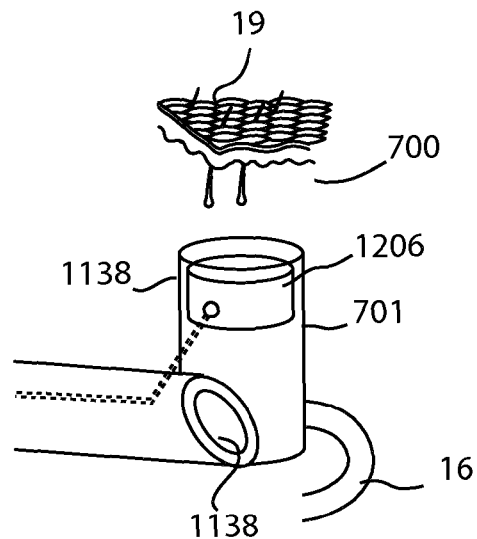
FIGS. 23A-23D are side views of another extraction module during hair follicle extraction.
Figure 23B:
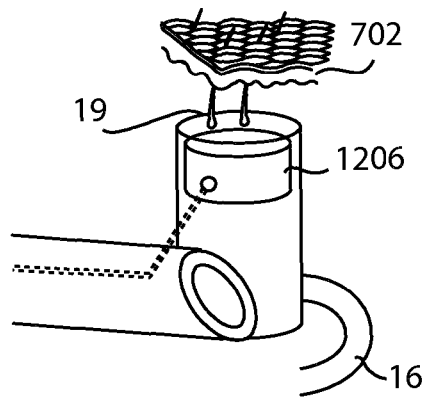
Figure 23C:
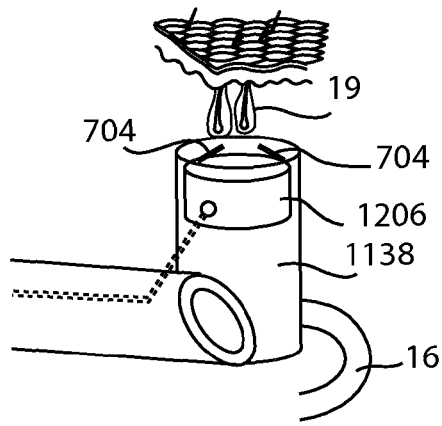
Figure 23D:
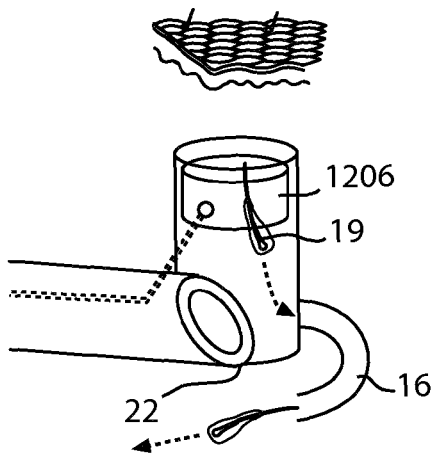
Figure 24:
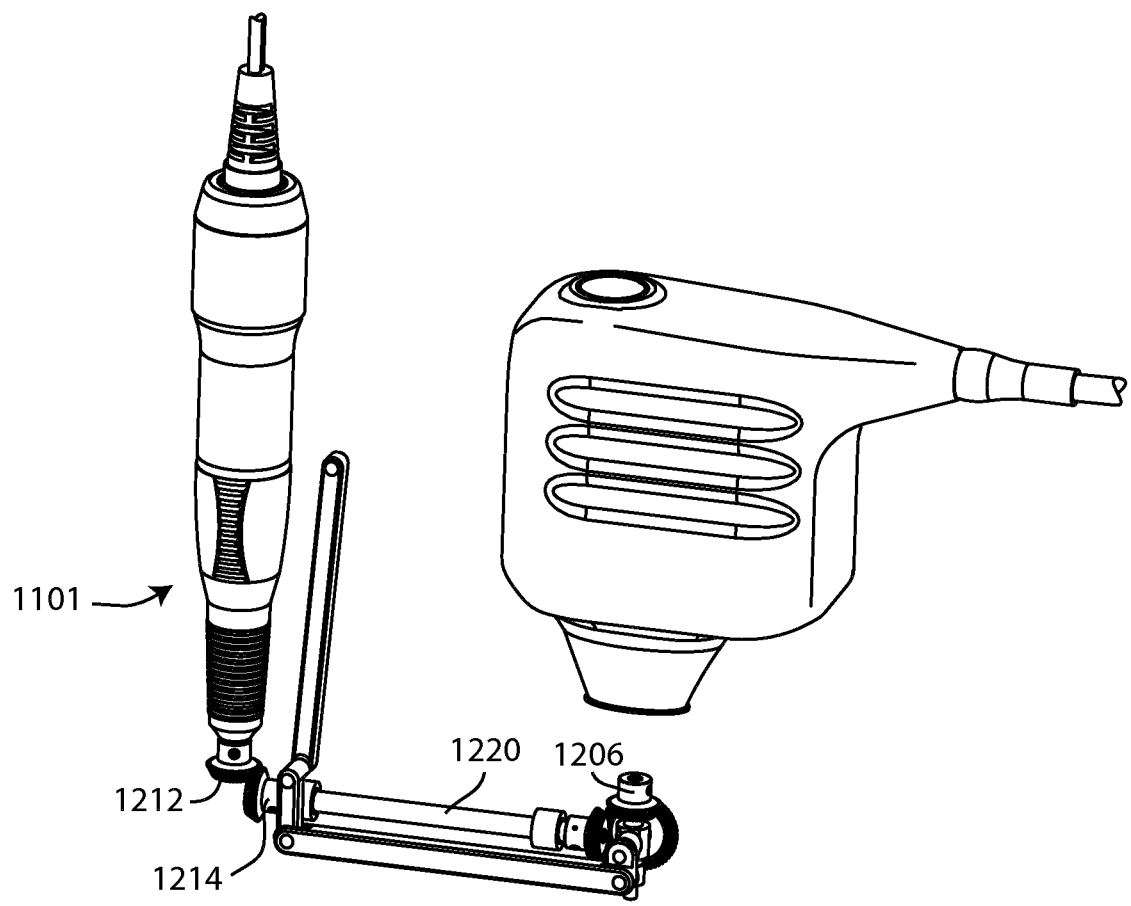
FIG. 24 is a top perspective view of a gear assembly in an instrument for follicular unit extraction.
Figure 25:
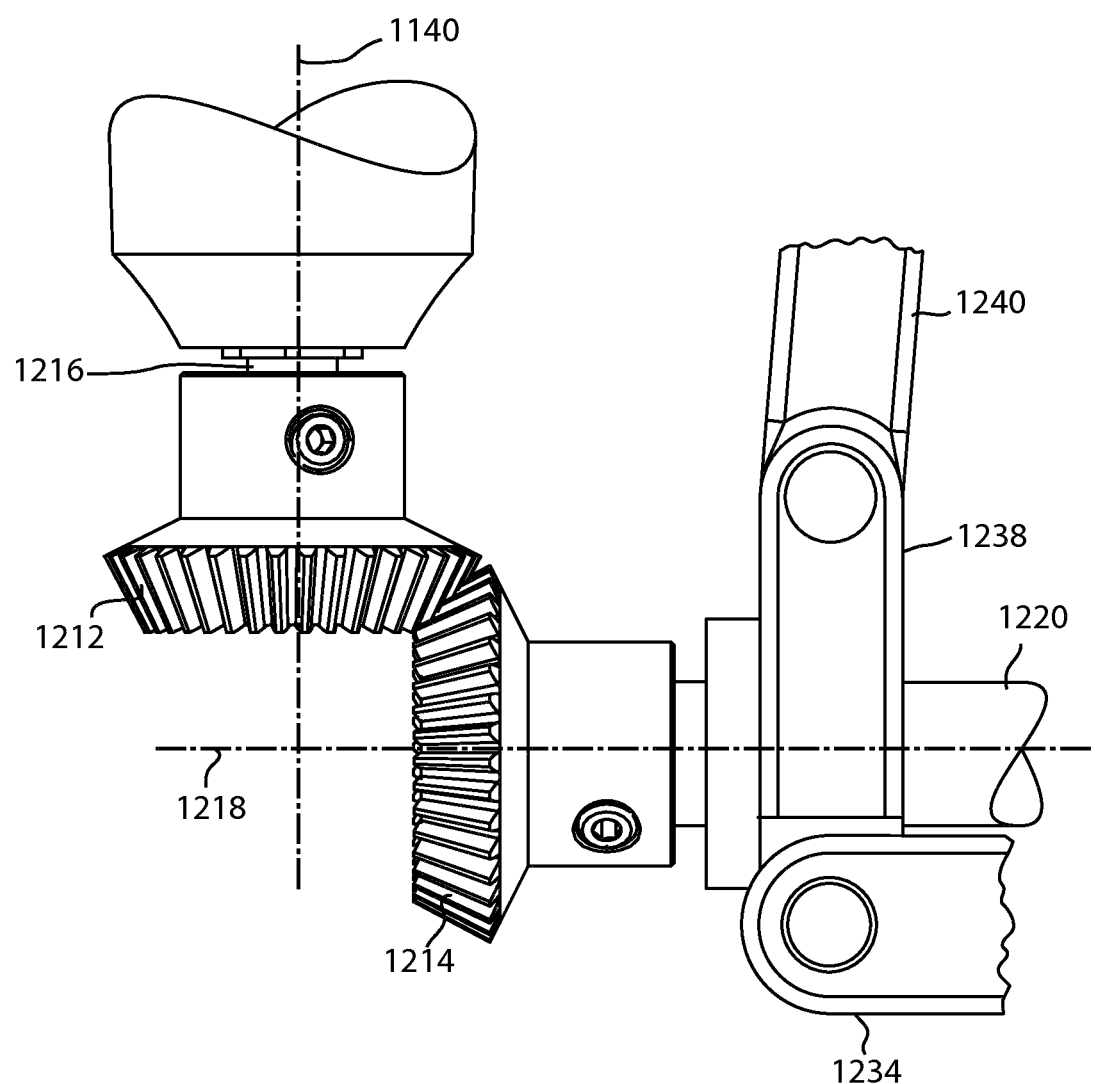
FIG. 25 is a side detail view of a portion of the beveled gear assembly of FIG. 24.
Figure 26:
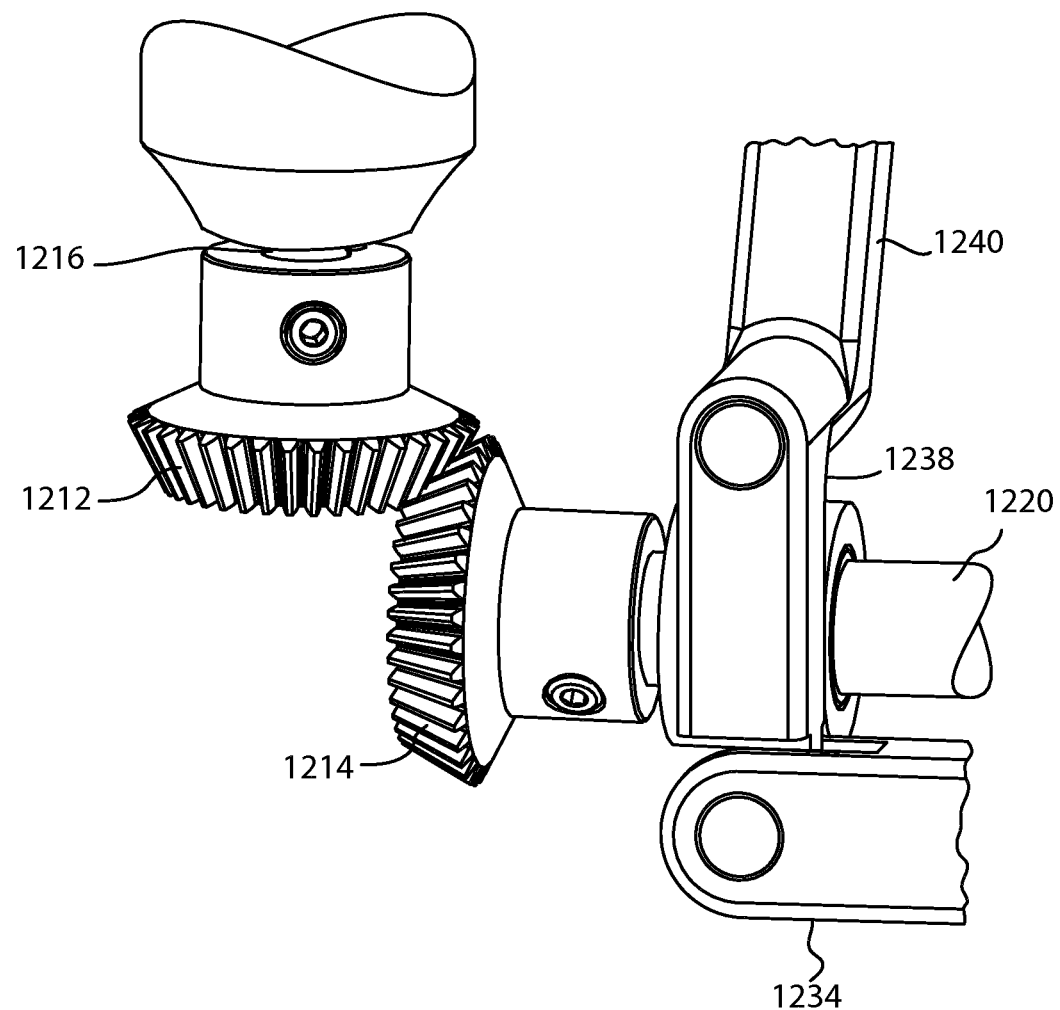
FIG. 26 is a top perspective detail view of the beveled gear assembly of FIG. 25.
Figure 27:
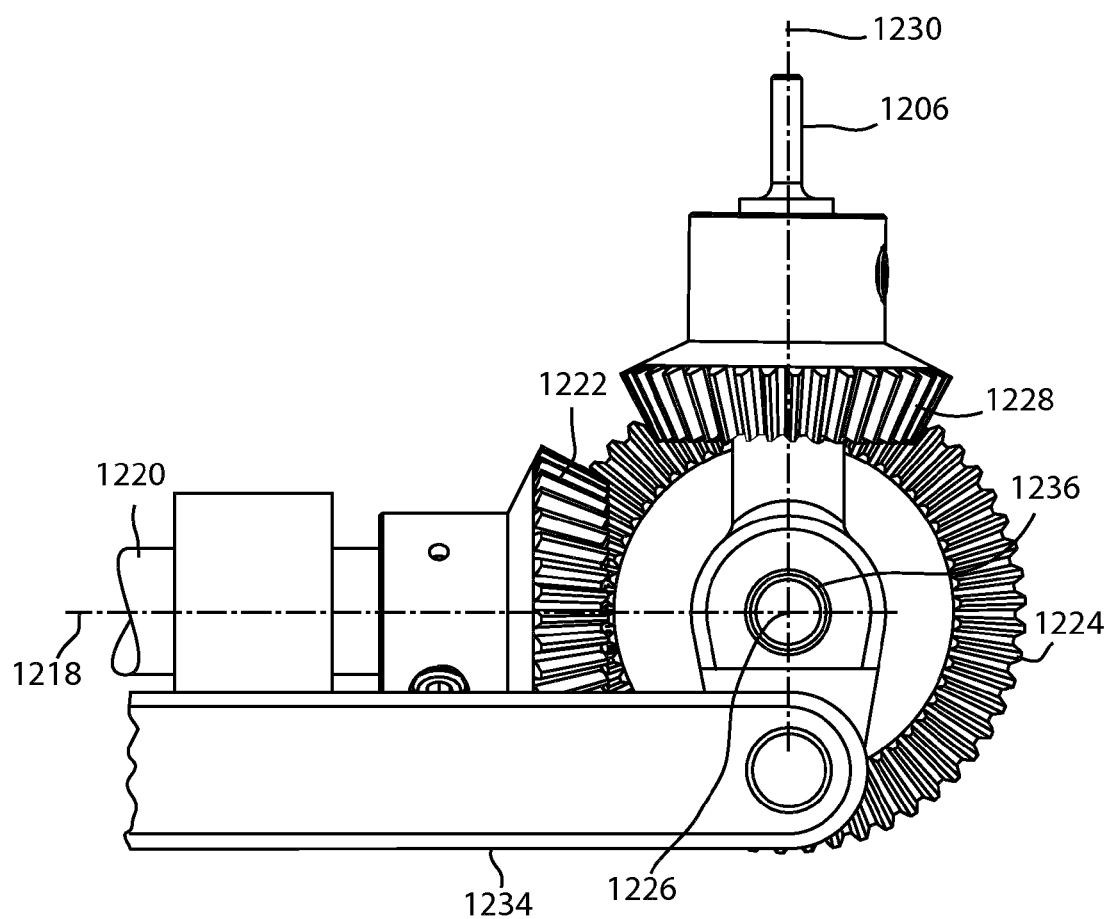
FIG. 27 is a side detail view of another portion of the beveled gear assembly of FIG. 24 in a first position.

The tissue removal component 1138 may also include a saline flush feature in order to facilitate removal of the clipped target tissue away from the extraction site. The saline flush feature (not shown) may be coupled with the suction portion. A saline solution may be injected near the extraction site prior to a tissue removal procedure to expand the tissue. Saline solution injected at the time of coring and clipping may also help to lubricate the suction tubes in order to more easily slide the clipped target tissue through a removal port after extraction. Saline solution, with or without one or more additives, may furthermore facilitate healing of the extraction site, inhibit infection, relieve pain, reduce scarring, and/or relieve swelling. Referring to FIG. 23D, an isolated follicular unit (FU), or micro-graft, 706 including intact hair follicle 19 and any attached peri-follicular tissue is illustrated being driven into moistened vacuum tubing 16 by a vacuum force 27 (in FIG. 8) and an irrigation jet of sterile saline (for instance, 0.5.mL-1.5 mL of saline) ejected from a saline port 22 near distal end 500 of endoscope 1 when activated by trigger 7.

The saline solution may be injected from a subcutaneous injection port, or may otherwise be injected via an external needle near the site of the target tissue extraction.

The suction portion may be designed to remove a target tissue after coring and clipping. The suction portion may encompass at least a portion of the tissue removal component, and may be also configured to apply suction to the target region of tissue in order to help stabilize the target tissue and/or move the target tissue toward the extraction module before the target tissue is cored and clipped. The suction port may be in fluid communication with a reservoir that receives that target tissue that after extraction and removal by the tissue removal implement.

Referring to FIGS. 35A-35D, a cored micro-graft 706 including the isolated intact hair follicle 19 is shown being dragged through moistened suction tubing 16, through an entrance port 25, and towards an isolation container 28. Multiple isolation containers 28 may be used, each accepting a different category of FU (e.g., determined based on the number and/or caliber of intact hair follicles contained in the FU). In order to separate the FUs into the appropriate isolation containers, a sensor 900 positioned along tubing 16 identifies and categorizes each FU based on the number and caliber of intact hair follicles it contains. The hair is comprised of keratinized protein, which distinguishes it from surrounding tissue and allows the sensor 900 to identify and quantify the number of hair structures in a given micro-graft 706. Note that in the context of this disclosure, an intact hair follicle is defined as a hair follicle that contains sufficient amounts of both stem cell containing regions (i.e., the bulb (dermal papilla) and the bulge region (within the isthmus) that are required for hair follicle self-renewal. The structural connection between the bulb and the bulge within a follicle must be in communication for the follicle to be considered intact. Sensor 900 may operate alone, or in combination with hardware and/or software algorithms for FU categorization.

Sensor 900 activates a separation device 902, triggering the opening of a gate 904 corresponding to the appropriate isolation container 28 and allowing the FU to reach its appropriate isolation container. The separation device 902 may also include a series of sieves that may separate the incoming follicular units based on size. The separation may be activated by a suction force that is greatest along the path toward the selected isolation container.

Referring to FIG. 13, each isolation container 28 may contain a sterile collection pool 23 of preservation solution (e.g., normal saline, oxygen- and ATP-enriched solution, etc.) chilled to a temperature range of 1-10° Centigrade. The collection pool may be similar to the Schuco® Suction Canister and the vacuum source 27 used to generate suction pressure may be akin to Schuco® Vac. Vacuum source 27 provides the vacuum used to help isolate intact FU 706, as described above. The vacuum pressure ranges from 50-300 mm Hg. A filter 26 positioned between vacuum source 27 and isolation container 28 maintains the sterility of collection pool 23. A barrier 24 (typically about 2 cm in height) located near entrance port 25 helps to ensure that grafts 706 drop downwards into collection pool 23 rather than being pulled toward vacuum source 27.

In the example shown in FIGS. 14-19, the external reference module 1106 may be removably attached to the first arm 1108 of the "C-shaped" member 1102, and may include a rod or a transdermal visualization detection device. When the external reference module 1106 is connected to the first arm 1108, the external reference module 1106 may be at least partially contained within the elongated slot 1117 on the curved portion 1118.

As illustrated in FIG. 14, an example of the external reference module 1106 may include a probe with an elongated rod portion 1107 and a pointed distal tip 1109. The external reference module 1106 may be hollow, or may otherwise be solid. The external reference module 1106 may be removably attached to the first proximal arm 1108 of the C-shaped member 1102.

Referring to FIGS. 36-38, the external reference module 1106 may include at least one pin 1130 or other extension that is shaped to be at least partially received within at least one guide slot 1132 on the curved guide portion 1118 of the first proximal arm 1108. In the example shown in FIGS. 36-38, the first proximal arm 1108 includes two guide slots 1132 shaped to receive two pins 1130 of the external reference module 1106. The external reference module 1106 may be slidable along a track defined by the guide slots 1132. To facilitate movement of the external reference module 1106 along the guide slots 1132, the external reference module 1106 may be attached to a linkage system 1134 that is contained substantially within the body of the C-arm 1102. The linkage system 1134 may include a plurality of hinges 1136 and may also be attached to a portion of the extraction module 1104 that is contained within the second distal arm 1110 of the C-arm 1102. The linkage system 1134 with hinges 1136 may be rotatable and may be manipulated by an operator to facilitate the movement of the external reference module 1106 along a defined pathway, as illustrated in FIGS. 36-38. When the external reference module 1106 is manipulated by an operator to move within the guide slots 1132, a central axis of the external reference module 1106 may remain in alignment with a central axis of the extraction module 1104, as illustrated in FIGS. 36-38. In some examples, the axes may be maintained in a coaxial alignment during manipulation.

The guide slot 1132 is one example of a guide feature which may interact with and control the position and orientation of the external reference module 1106. Other types of guide features may include rails, beams, grooves, channels, edges, holes, protrusions, recesses and the like.

Figure 17:
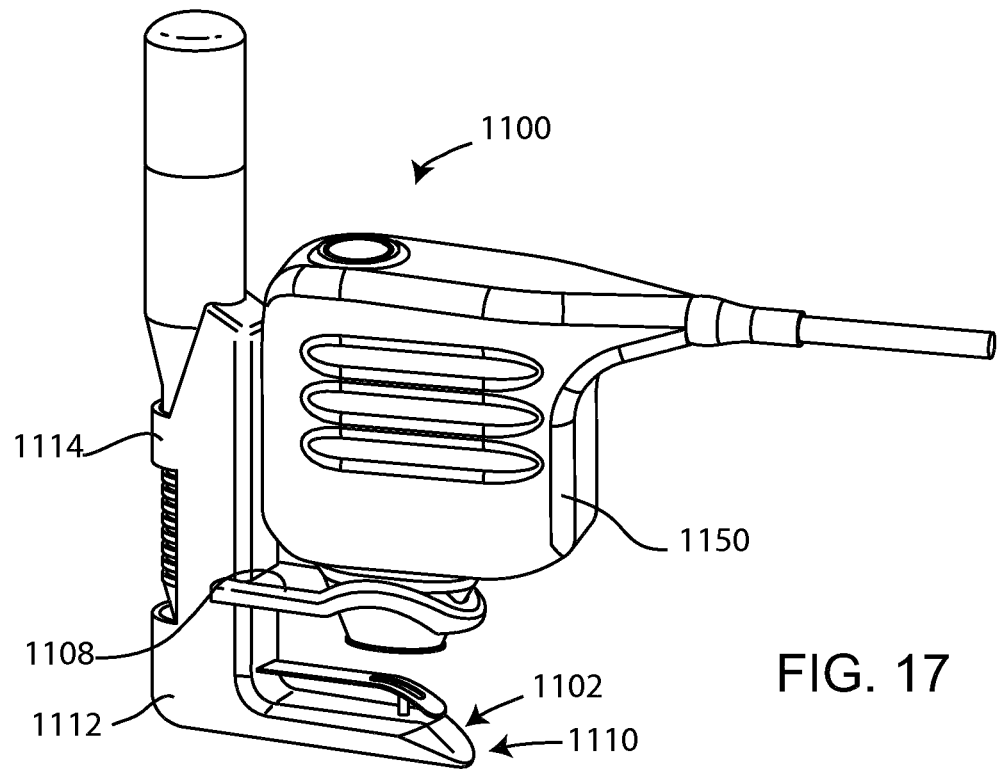
FIG. 17 is a side perspective view of the instrument of FIG. 16 with a different transdermal visualization module.
Figure 18:
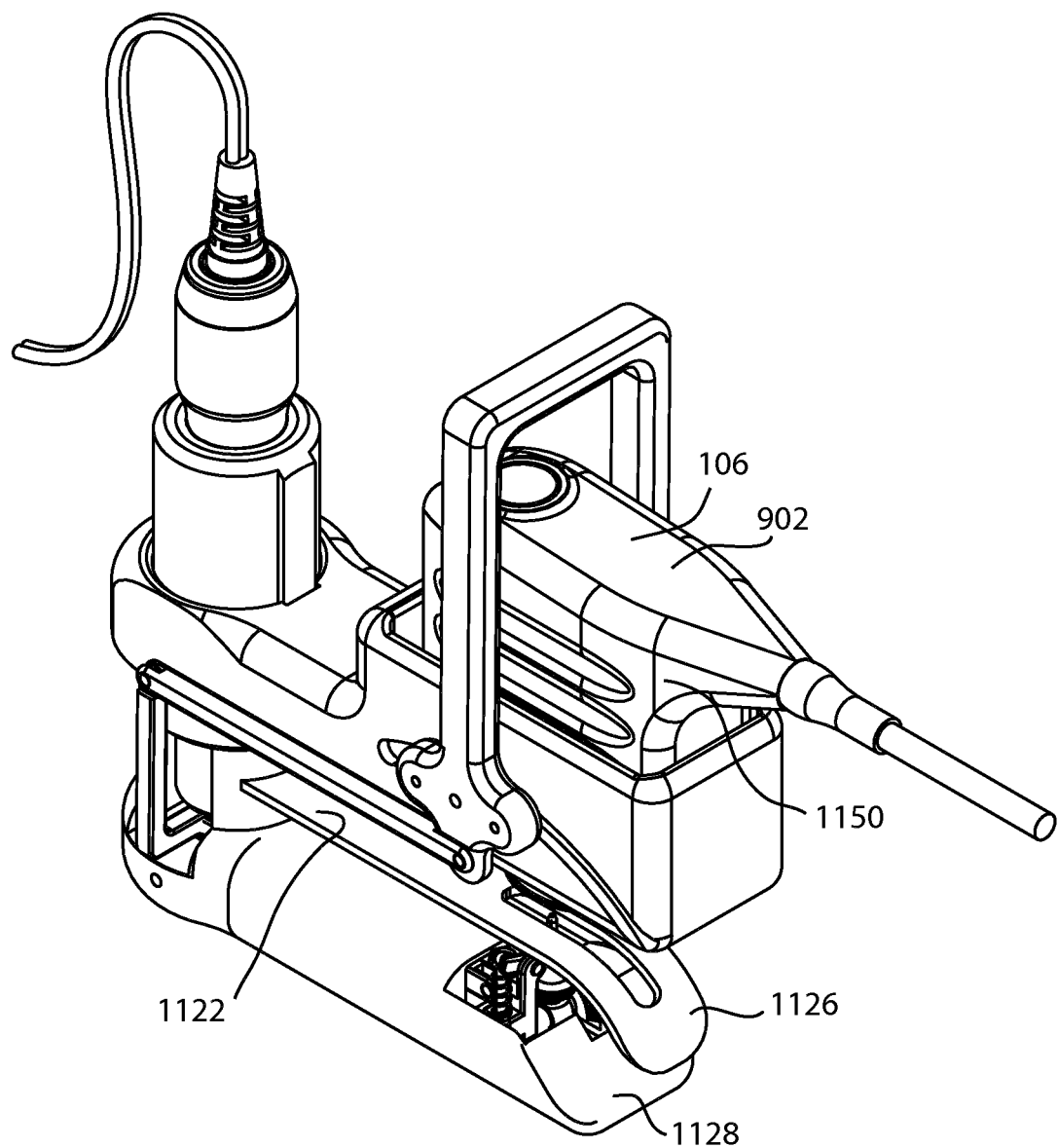
FIG. 18 is a top perspective view of the instrument and transdermal visualization module of FIG. 17 with an external frame.
Figure 19:
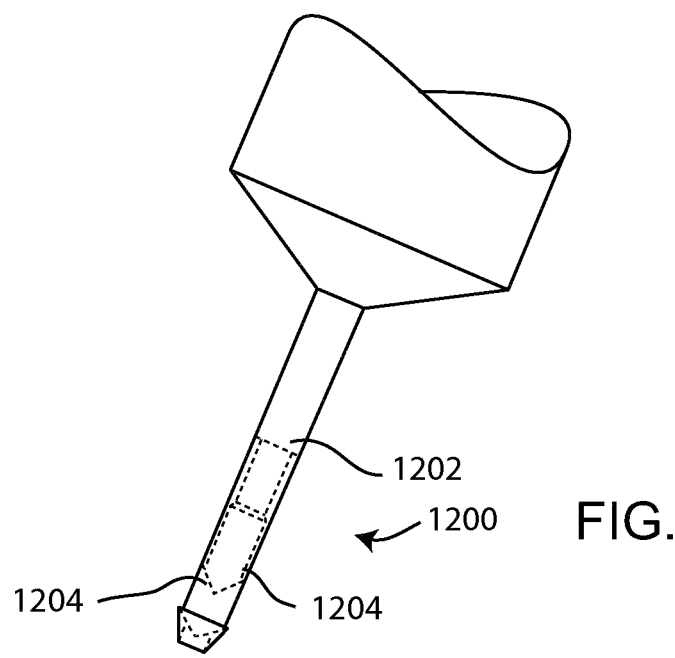
FIG. 19 is a side view of a coring and clipping module.

Alternatively, the external reference module 1106 may include a transdermal visualization or transdermal detection device 902 1150 as illustrated in FIGS. 17 and 18. The transdermal detection device may provide an assessment of the detailed layout of tissue types beneath the skin surface. In one example, the transdermal detection device may be a bright, minimal-heat emitting external light source (such as a halogen bulb with a dichroic reflector that reduces heat in the light beam by nearly 70% by transmitting the infrared radiation, or heat, backwards). In another example, the transdermal detection device may be an ultrasound device. The ultrasound (30-50 MHz frequency) may enable detailed visualization of the tissue of interest within approximately 1-7 mm beneath the skin surface. In FIG. 8, a probe, similar to external reference module 1106 is illustrated with an integrated ultrasound device. The probe is illustrated viewing a follicle portion beneath the skin surface. In other examples, selective visual enhancement may be achieved using visual isolation techniques that take advantage of the unique biological structure and/or properties of hair follicles (e.g., absorption or reflection characteristics of light or magnetic properties).

Figure 16:
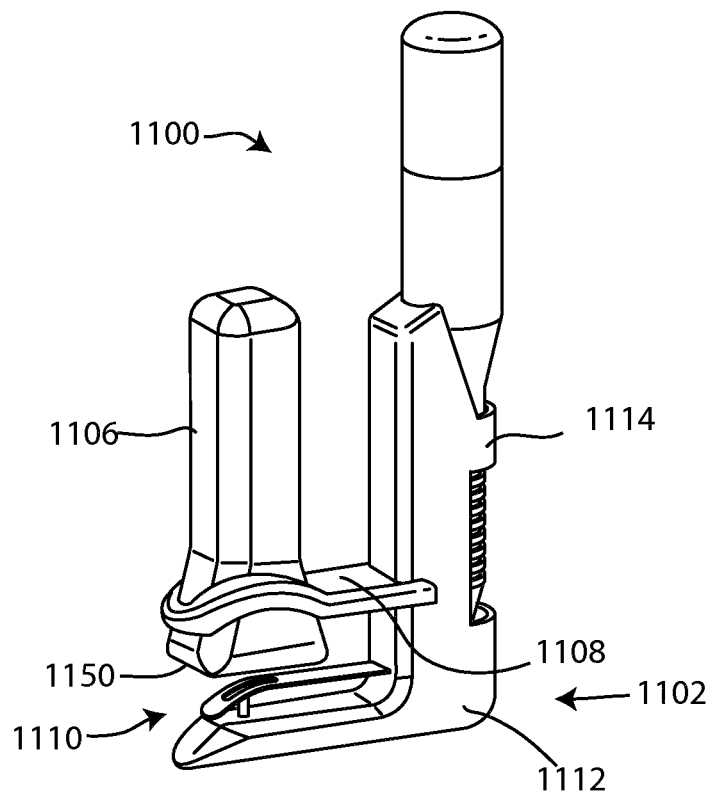
FIG. 16 is a perspective view of another endoscope instrument follicular unit extraction with a transdermal visualization module.

In the example shown in FIGS. 17 and 18, the transdermal visualization device 1150 is an ultrasound device, which may also be referred to as an ultrasound probe. The ultrasound probe may be removably attached to the proximal first arm 1108, as illustrated in FIGS. 16-17. During use, the ultrasound device may rest against the skin surface from outside of the body.

If the visualization component 1150 of the endoscope 900 lies on the opposite side of the skin surface from the active engagement component (i.e., the tissue extraction device 1104), the bridging component 1112 may use any of various types of connections, including, for instance, a direct transdermal bridge at the site of interest, an indirect transdermal bridge crossing the skin surface at an alternate site, a magnetic connection, a connection utilizing lasers or radioactive or ultraviolet waves, a connection formed by chemical or gaseous bonds, or a connection established by structural changes to the skin surface initiated from the opposite side of the skin.

The connection stabilizes movements between the visualization device 1150 and the tissue extraction device 1104 that actively engages the tissue of interest. As many forms of visualization (e.g., ultrasound) display in two dimensions (X and Y axes) while neglecting the third axis (Z axis, or depth of viewing field), this connection effectively "locks in" the tissue of interest by eliminating the possibility that the tissue of interest strays into or out of the Z, or depth of view, axis.

The ultrasound probe may be manipulated by an operator, and may be used to create a visualization field, which relays information regarding a target hair follicular unit or other target tissue, as well as the surrounding tissue. The information may include the size of the follicle, the number of individual follicles within a follicular unit, the depth and orientation of the follicle, and information regarding the surrounding tissue. Additional information may include the angle of the hair follicle, and any curl characteristics of the hairs contained in a follicular unit. Based on the information gathered by the visualization device, an operator may then manipulate the extraction module 1104 along an interior tissue surface to the site of the target tissue and effectively remove the target tissue.

In one example method of use of instrument 1100, an operator may create an incision within the donor area that is shaped to accommodate the insertion of the second distal arm 1110 and/or middle portion 1112 of instrument 1100. The operator may use an additional barrier device to separate the epidermal layer from the subcutaneous tissue and create a visualization cavity, such as a balloon device or blunt dissector. Alternatively, the beveled edges 1126, 1128 of the platform 1122 and base 1120 respectively, may facilitate the adequate separation of the epidermal layer from the subcutaneous tissue to insert at least a portion of the second distal arm 1110 into the incision, such that the extraction module 1104 lies beneath dermal tissue and the external reference module lies near an exterior tissue surface. Once the base 1120 has been inserted into the incision, the instrument may be manipulated by an operator to externally identify and locate a target tissue for removal. The instrument 1100 may be rotatable about the axis 1140 defined by the middle portion 1112 and proximal handle 1114. The operator may rotate or slide the instrument 1100 within the incision, and may manipulate the external reference module 1106 such that the external reference module 1106 moves along the scalp surface in order to identify tissue that is desirable for removal from the donor area. The operator may use the external reference module to identify the target tissue and to adequately align the extraction module with the hair follicle.

For example, the probe illustrated in FIG. 14 may be used by an operator to align the extraction module 1104 with a target follicular unit by pointing the tip 1109 at the target tissue and optionally aligning the probe shaft with a hair shaft. The external reference module 1106, in this example the probe, can be any mechanical device used to provide a line-of-sight and an external reference point. The tip 1109 may then be pressed downward to urge the target tissue into contact with the extraction module that lies beneath the tissue. The operator may then actuate the instrument 1100 such that the tissue removal implement 1138 excises the desired follicular unit from the internal surface of the epidermal layer by coring around the intact follicular unit and clipping the follicle in order to separate it from the overlying skin surface at a predetermined distance from the skin surface (often less than 1 mm). Alternatively, to excise the follicular unit, the tissue removal implement 1138 may be pressed upwards against the underside of the skin surface. When the removal implement 1138 is pressed upwards, it may approach, but not pierce, the overlying skin tissue.

In another example, the external reference module 1106 may include the ultrasound device, such as the example shown in FIGS. 17 and 18. The operator may turn on the ultrasound device to develop the visualization field and gather information regarding the target tissue. Example methods for activating an ultrasound unit include pressing a foot pedal that is connected to the ultrasound unit, pushing a button within the ultrasound unit, or using a connected computer system to active the ultrasound unit. Once the operator has identified and assessed the target tissue area (for example a follicular unit) for removal, the operator may then align the extraction module by engaging a trigger or toggle to appropriately engage the target tissue. In some examples, the extraction module may be coupled to the external reference module so that once the operator has positioned the external reference module to identify and assess the target tissue area, the extraction module is appropriately positioned to extract the target tissue. The operator may then turn on the motor unit, which actuates the rotation of the coring cannula 1206 via the geared linkage system described previously. The coring cannula 1206 may move to surround and create a core around the target tissue.

Once the target tissue has been identified and the extraction module has been aligned with the target tissue, the target tissue may be cored and clipped. The suction port may then facilitate removal of the excised follicular unit by drawing the follicular unit away from the site of excision along a suction pathway that includes tubing within the base 120 and towards a storage vial or reservoir 144 that is outside of the human body. The suction tubing and reservoir may contain a saline flush solution, as well as various other preservative or biological solutions for maintaining the viability and stability of the follicular units such that they remain viable for reimplantation at the recipient area.

The collection of isolated micro-grafts 706 contained in pool 23 of preserving solution may subsequently be separated further manually based on follicle characteristics such as number of hairs per FU and/or caliber of each individual hair. Each FU bundle 706 may be sent to one of the following collection troughs: fine, single-haired FU; coarse, single-haired FU; fine, two-haired FU; coarse, two-haired FU; fine, three-haired FU; coarse, three-haired FU; and follicular families (FF) containing clusters of more than three hairs per FU.

After the desired number of intact FUs have been effectively removed from the patient, the barrier device and endoscope 1100 may be removed from the visual cavity beneath the patient's scalp. Afterwards, the incision into which the endoscope and its attachments were introduced is sutured closed using, for example, 5-0 nylon sutures in a continuous running suture so as to leave a nearly imperceptible scar in a hidden post-auricular zone. The scar may be linear, curved, lobular, zig-zag, radiate, or other shape.

The suction may be applied continually throughout the procedure, or may be actuated after the target tissue has been clipped.

In another example of instrument 1100, the C-arm may accept the external reference module 1106 and extraction module 1104 interchangeably, such that the external reference module 1106 is attachable to the distal second arm 1110 and the extraction module 1104 is attached to the proximal first arm 1108. In another example of instrument 1100, the proximal arm 1108 and the distal arm 1110 may be separate components, wherein the distal arm 1110 may include a tissue extraction module 1104 and may be inserted subdermally, while the proximal arm component is used on an exterior surface as a reference guide 1106 for the subdermal extraction. Other methods for tissue excision may also be contemplated, such as the use of lasers to cut around the target tissue.

Figure 39:
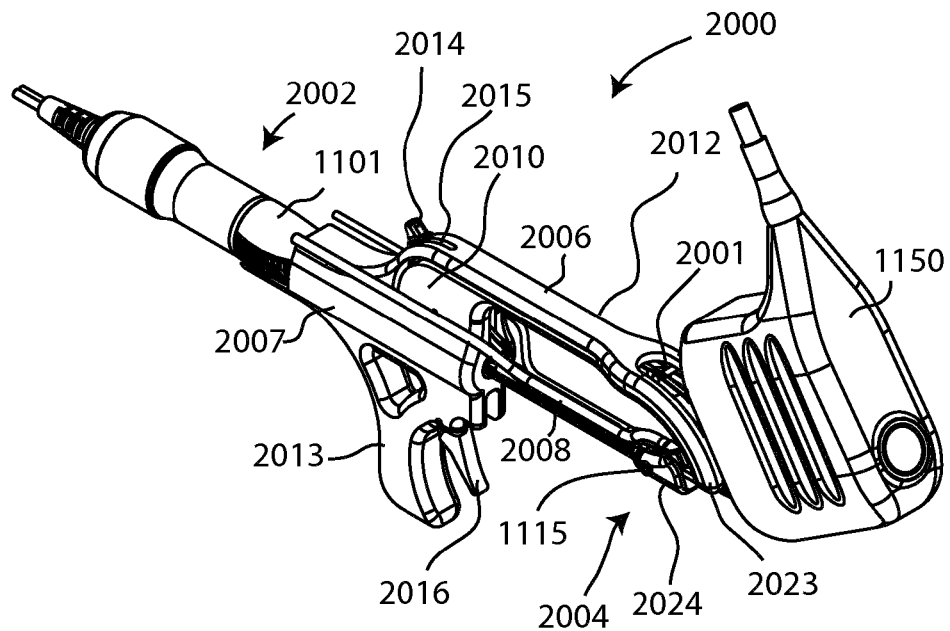
FIG. 39 is a top perspective view of another endoscope instrument with a visualization device attached.
Figure 40:
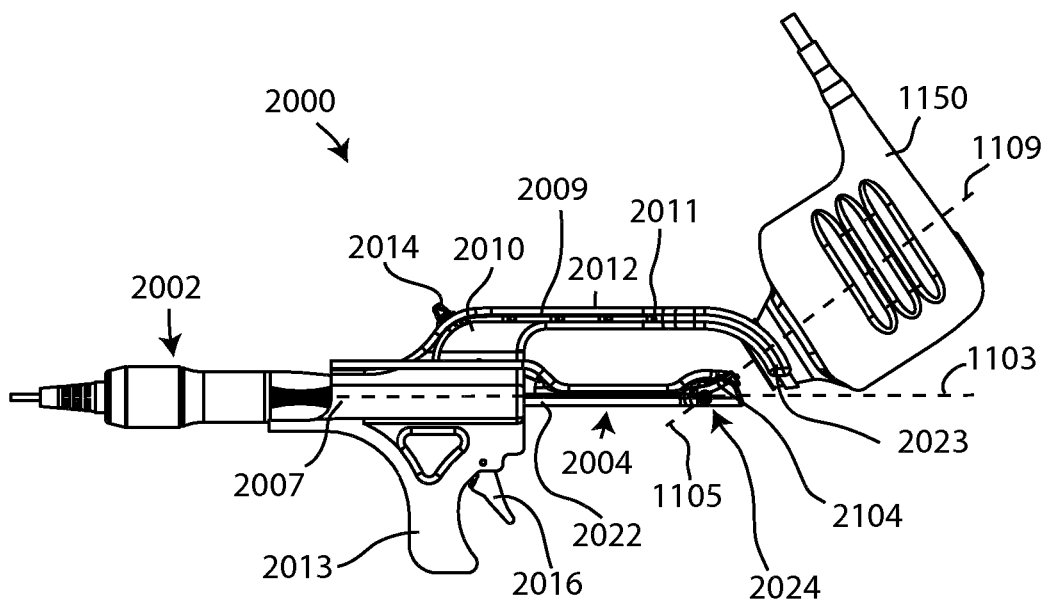
FIG. 40 is a side view of the instrument of FIG. 39.

Referring to FIGS. 39-40, another example of an instrument for tissue removal is illustrated. Instrument 2000 may have similar features to instrument 1100. Instrument 2000 may include a proximal portion 2002, a middle portion 2007, which may also be referred to as a bridging component, and a working end 2004. The middle portion 2007 may be located between the proximal portion 2002 and the working end 2004. The proximal portion 2002 may be coupled to a motor unit, similar or identical to motor unit 1101 described previously. The working end 2004 may include a first arm 2006, and a second arm 2008 that is substantially parallel to the first arm 2006. The second arm 2008 may also be referred to as a sub-dermal arm. The first arm 2006 and the second arm 2008 may extend from the middle portion 2007.

The first arm 2006 may include a rounded shoulder portion 2010 that is congruent with the middle portion 2007 and an elongated prong 2012 that extends from the shoulder portion 2010. The elongated prong 2012 may include an aperture 2001 or other guide feature for receiving a visualization module, such as the ultrasound device 1150, as illustrated in FIG. 39. The aperture 2001 may be located on a rounded end portion 2023 of the prong 2012. When the visualization component 1150 is mounted on the rounded end portion 2023, the visualization component 1150 is moveable within the aperture 2001. As the visualization component 1150 is moved within the aperture 2001, the angle of a central visualization axis 1109 may vary with respect to a longitudinal axis 1103 that extends along the second arm 2008. The aperture 2001 may control or guide the angle of axis 1109 as the visualization component 1150 moves. The visualization module may otherwise be an alternative external reference device, such as rod 1107 described previously. In another example, the elongated prong 2012 may be attachable to a stereotactic frame or other external reference device.

Figure 41:
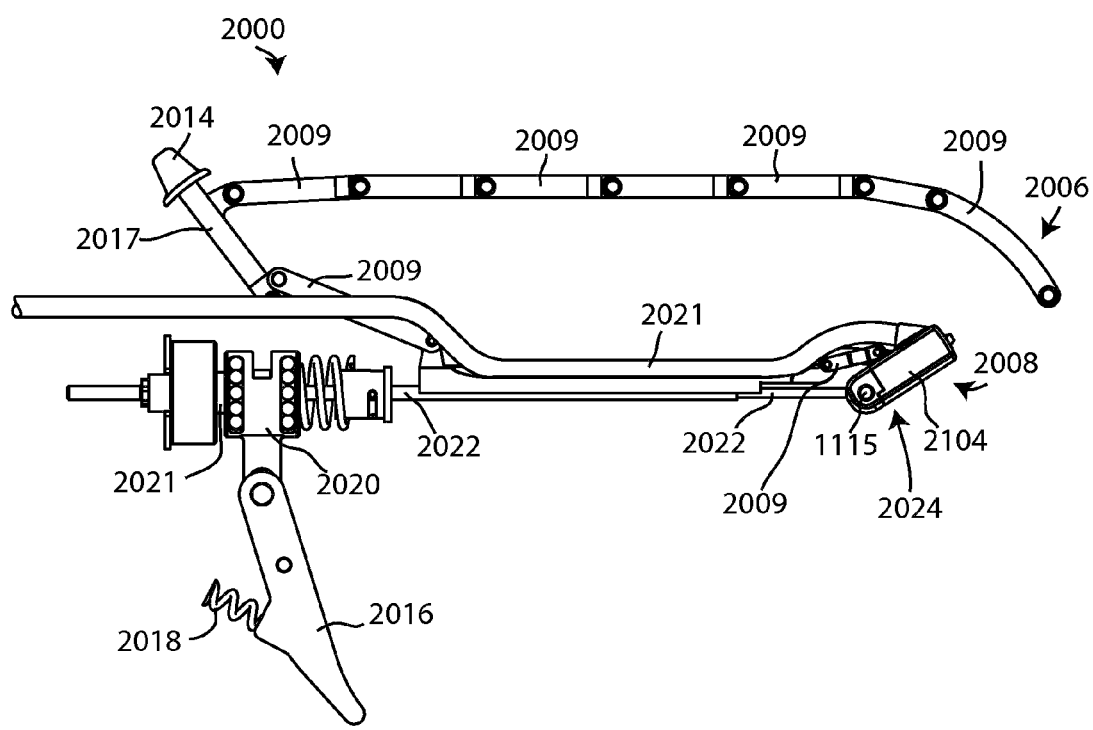
FIG. 41 is a side view of the linkage components of the instrument of FIG. 39.

As illustrated in FIG. 41, visualization module 1150 may be communicably coupled to an extraction module 2104 carried by the second arm 2008, through a series of linked bars 2009. The linked bars 2009 may be coupled to one another via hinges 2011. The first arm 2006 may also include a toggle 2014, which may also be a switch, button or other control element that is carried within a slot or groove 2015 on the shoulder portion 2010. The toggle 2014 may include a rocker bar 2017 that is connected to the linked bars 2009. The linked bars 2009 may be connected to the visualization component 1150, and may be carried by a track or channel within the first arm 2006, and further within an internal cannula of the second arm 2008 to connect to the extraction module 2104.

As the visualization module is manipulated within the aperture 2001, the central visualization axis 1109 may be aligned with a target hair follicle for removal. As the visualization module 1150 is manipulated, the movement of the visualization module is translated through the linked bars 2009 along the track to rotate the extraction module 2104 about an axis of rotation that is perpendicular to the visualization axis 1109. The axis of rotation may extend through a pivot member 1115, such as a pin or rod that extends through the base of extraction module 2104. As the extraction module 2104 is rotated, a central extraction axis 1105 remains aligned with the visualization axis 1109. The central extraction axis 1105 may be coaxially aligned with the visualization axis 1109.

Figure 42:
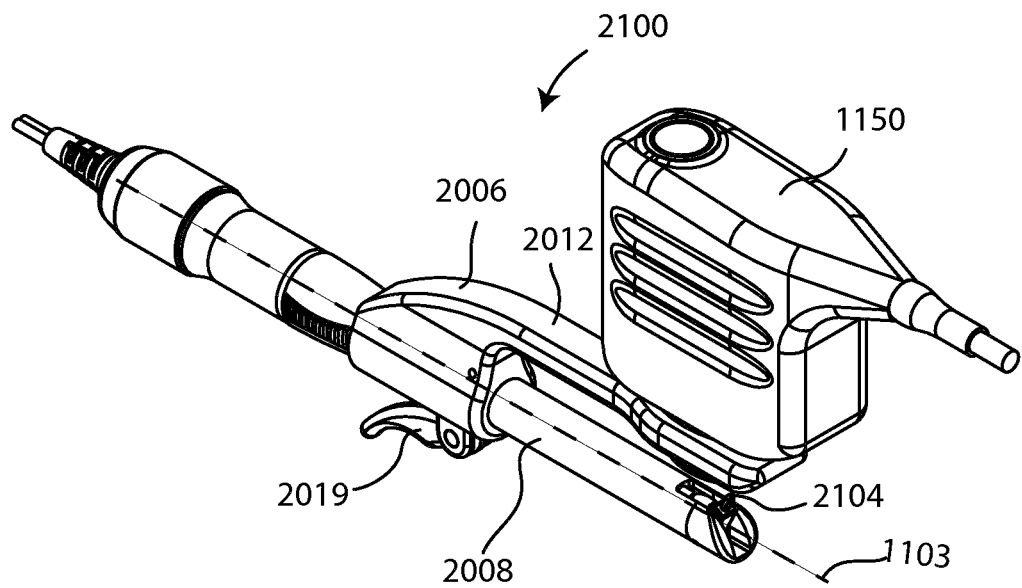
FIG. 42 is a top perspective view of another endoscope instrument with a visualization device attached.

The middle portion 2007 may also include a gripping handle 2013 that carries a trigger 2016 or other actuation component. As illustrated in FIG. 42, the trigger 2016 may include a spring component 2018, and may be connected to a carriage component 2020 within the middle portion 2007. The carriage component 2020 may carry a cylindrical housing with internal ball bearing components (not shown). The carriage component 2020 may be coupled to a drive shaft 2021 that extends from motor unit 1101, and may act to allow cable component 2022 to translate in response to actuation of the trigger 2016 while permitting cable component 2022 to be rotationally coupled to the motor component 1101.

The cable 2022 may be functionally connected to the extraction module 2104 that is located in the distal working portion 2024 of the second arm 2008. Extraction module 2104 may have similar or identical features to extraction module 1104 described previously.

Figure 44:
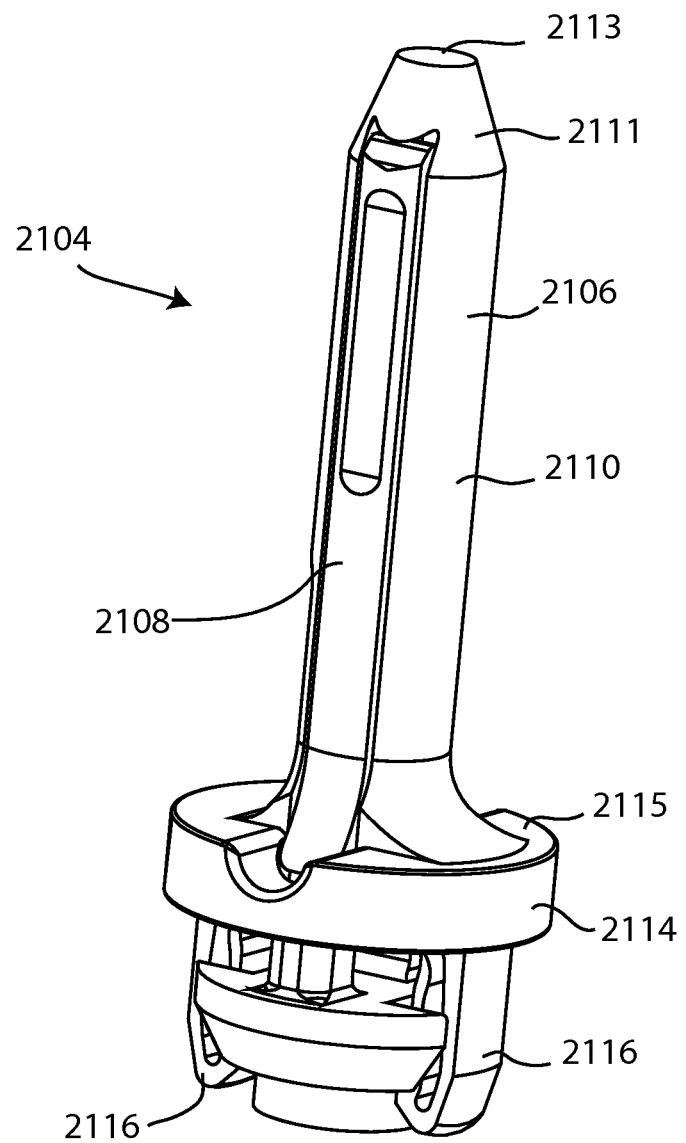
FIG. 44 is a perspective view of yet another extraction module.

Referring to FIGS. 44-50, another example of an extraction module is illustrated. Extraction module 2104 may include an external coring cannula 2106 and an internal clipping device 2108. When the extraction module 2104 is operatively assembled, the clipping device 2108 may be at least partially contained within the coring cannula 2106, as illustrated in FIG. 44.

Figure 45:
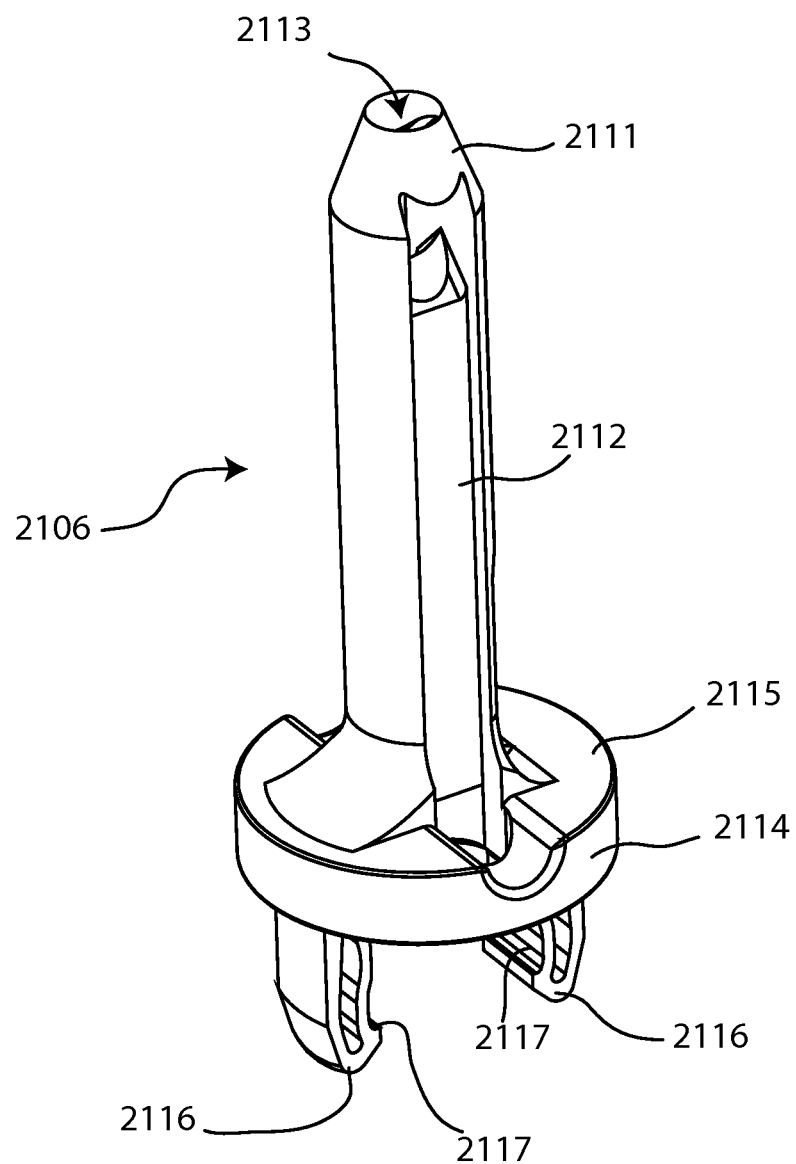
FIG. 45 is a top perspective view of a coring component of the extraction module of FIG. 44.
Figure 50:
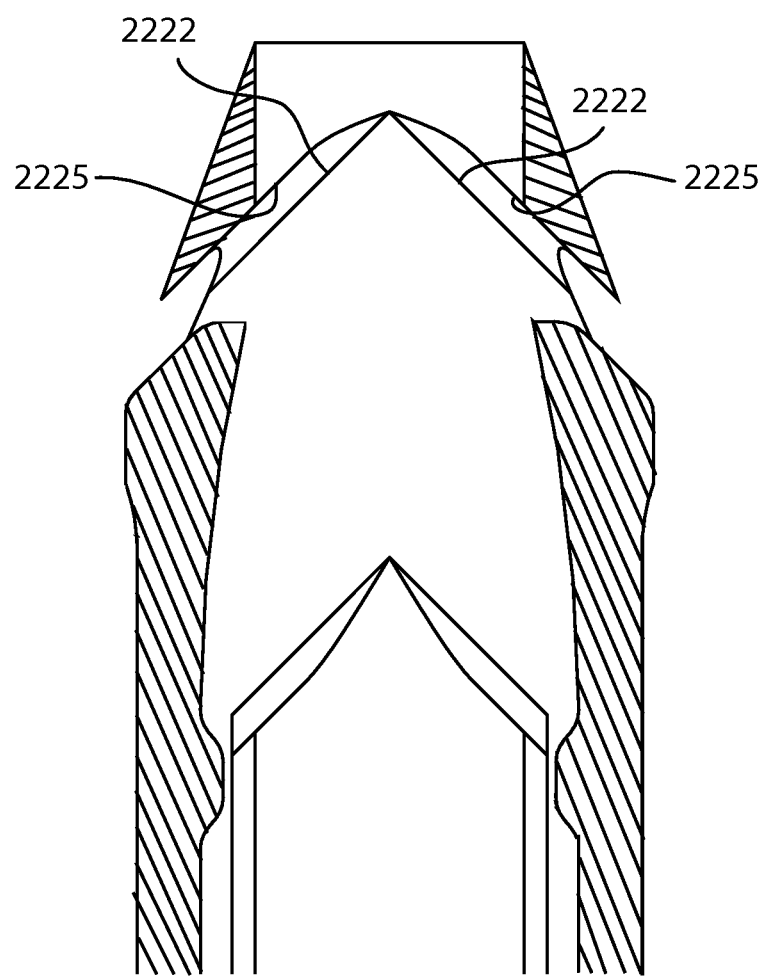
FIG. 50 is a cross section of the proximal portion of the extraction module of FIG. 44.

As illustrated in FIG. 45, the coring cannula may include a proximal shaft 2110 with two grooves 2112 or channels that extend along the shaft 2110. The proximal shaft 2110 may include a cone-shaped tip portion 2111 with a circular aperture 2113 at the end. The cone-shaped tip portion may include two interior beveled surfaces 2225, as illustrated in FIG. 50. The coring cannula may intersect a cylindrical base portion 2114 at a first surface 2115 of the cylindrical base 2114, which may also be referred to as a first stop feature.

Figure 46:
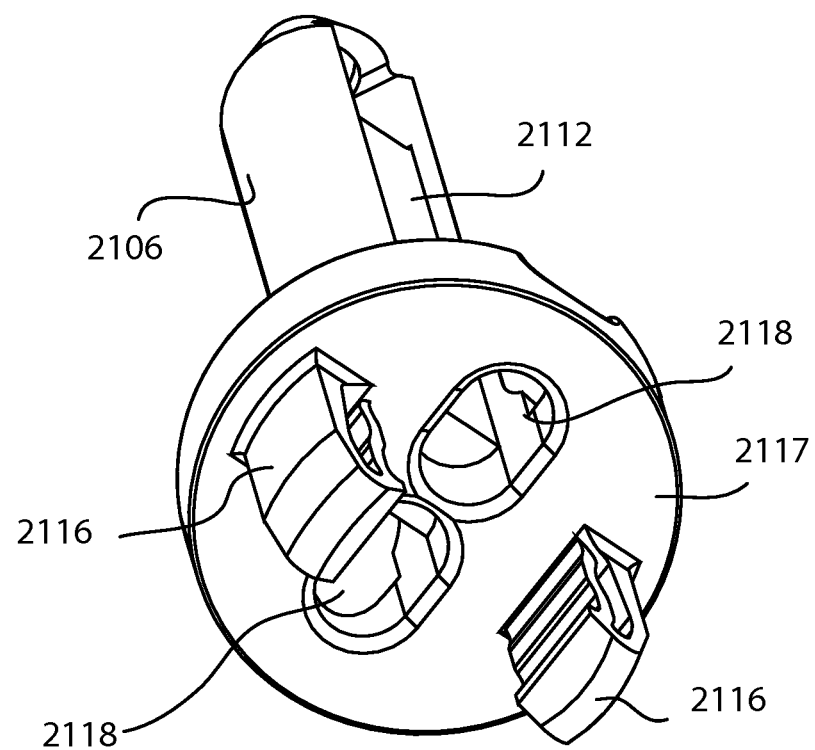
FIG. 46 is a bottom perspective view of the coring component of FIG. 45.

As seen best in FIG. 46, a plurality of clip spring elements 2116 may extend from a second surface 2117 of cylindrical base 2114. The second surface 2117 may be opposite to the first surface 2115. The cylindrical base 2114 may also include at least one aperture 2118 shaped to engage a portion of the clipping element.

Figure 47:
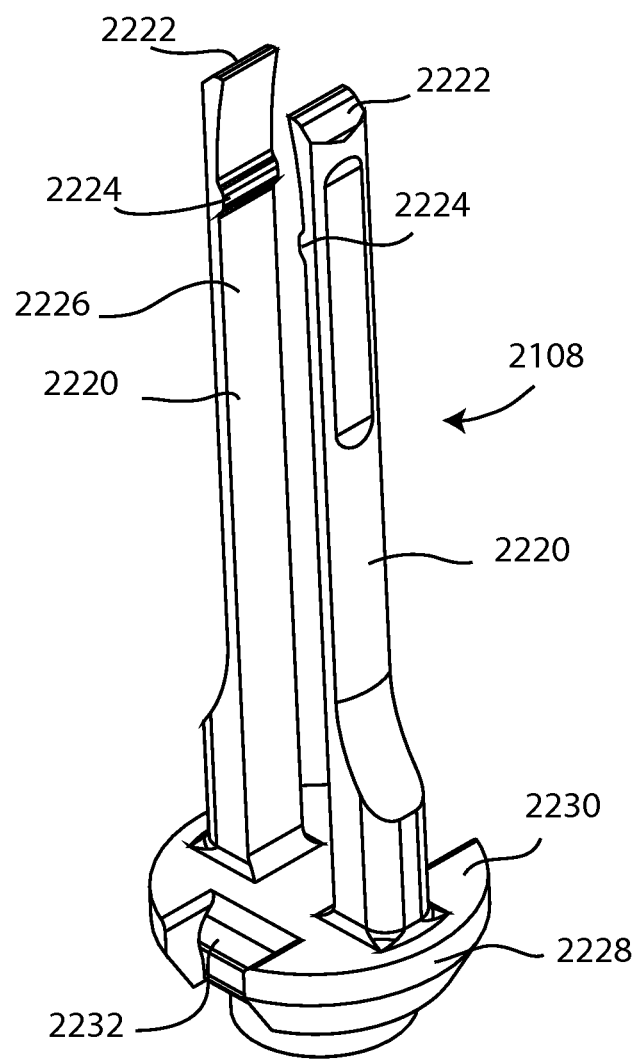
FIG. 47 is a top perspective view of a clipping component of the extraction module of FIG. 44.
Figure 48:
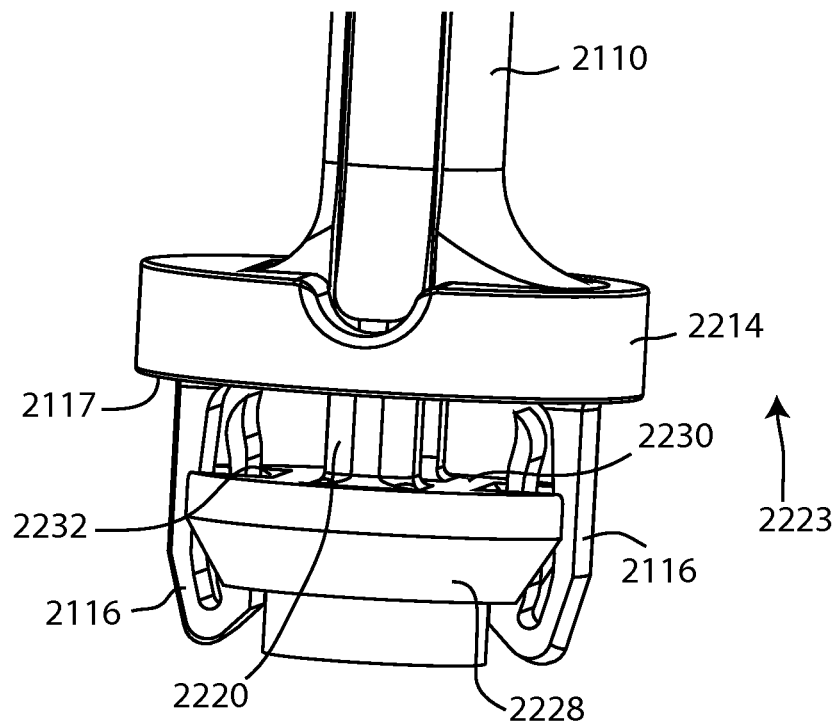
FIG. 48 is a side view of the distal portion of the extraction module of FIG. 44.

Referring to FIG. 47, the internal clipping element 2108 is illustrated. Internal clipping element 2108 may include at least one prong 2220. When the clipping element 2108 is assembled with the coring cannula 2106, the prongs 2220 may extend through the apertures 2118 on the cylindrical base 2114 and may be held in the grooves 2112 along the shaft 2110. The prongs 2220 may include proximal beveled edges 2222, and may include a tab feature 2224 on an interior facing surface 2226. The prongs 2220 may intersect a base portion 2228, which may be referred to as a second stop feature. The second stop feature 2228 may include a proximal surface 2230, and at least one cut-out portion 2232.

The coring cannula 2106 and clipping element 2108 may be located in an external housing element (not shown) that includes an interior ledge or other engagement feature. As seen best in FIGS. 44 and 48, when the coring cannula 2106 and clipping element 2108 are operatively engaged, the clip springs 2116 may be at least partially contained within the cut-out portions 2232 of the clipping element 2108. The clipping springs 2116 may include a first concave portion 2117 that holds the clipping element 2108 in a first position with regard to the coring cannula 2106. In the first position, which may also be referred to as a neutral or non-engaged position, the base portion 2228 of the clipping element 2108 does not contact the cylindrical base 2114 of the coring cannula.

In operation, as an operator activates the extraction module 2014, the coring 2106 and clipping 2108 elements may be advanced forward in the external housing (not shown) until the first surface 2115 of the cylindrical base 2114 contacts the ledge, which provides resistance to further movement of the assembly within the housing. Further force may then be applied via the trigger or other activation mechanism to overcome the spring bias provided by the clip springs 2116 to advance the clipping mechanism 2108 into a second position, as indicated by motion arrow 2223 in FIG. 48. The second position may also be referred to as an engaged position. In the second position, the proximal surface 2230 of the base portion 2228 of the clipping element 2108 may contact the second surface 2117.

Figure 49:
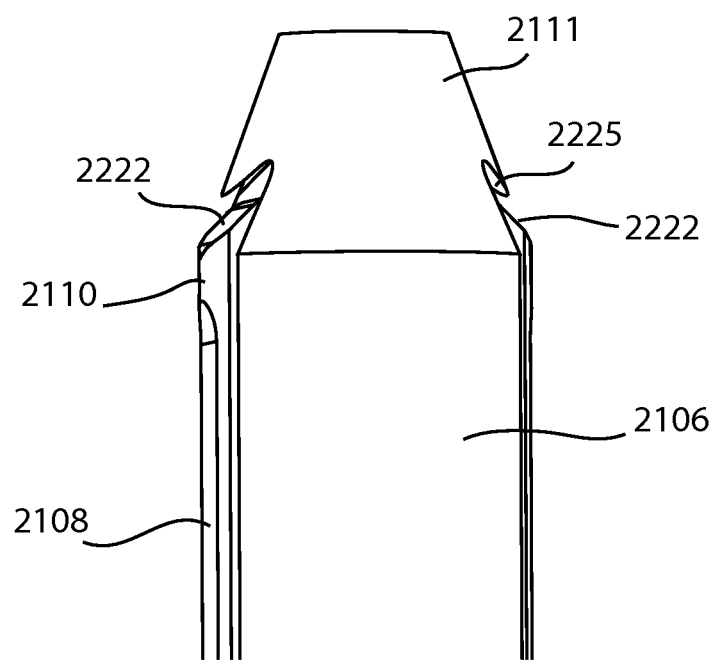
FIG. 49 is a side view of the proximal portion of the extraction module of FIG. 44.

As the clipping element 2108 is advanced within the coring cannula 2106, the proximal beveled edges 2222 of prongs 2220 may engage the complementary internal beveled surfaces 2225 of the coring cannula 2106, and may be urged towards one another to clip or cut out a piece of target tissue, as seen best in FIGS. 49 and 50.

After a target tissue has been clipped, a user may then retract the clipping element 2108 within the coring cannula 2106. As the clipping element 2108 is pulled back within the coring cannula 2106, the tabs 2224 may help to urge the prongs 2220 away from one another to release the clipped target tissue such that it may be pulled away into a suction port located in the housing (not shown) and along a removal pathway, such as tubing 16.

In an example of use of instrument 2000, a user may create a ½"-1" incision in the scalp of a patient using a dissection module, and then insert the second arm 2008 into the incision. The dissection module may be blade 10, which may be operatively assembled with instrument 2000, or a separate component. Second arm 2008 may be flexible such that as the second arm 2008 is inserted into an incision, the second arm 2008 may flex to match the contour of the skull as the second arm 2008 is moved towards a target hair follicle. The user may manipulate the visualization component, for example ultrasound device 1150, by grasping the visualization component and manually rocking the component within the aperture 2001 in order to identify and gather information about the target hair follicle for removal, for example, the angle of the follicle within the dermal and sub-dermal layers. Alternatively, the user may manipulate the toggle 2014 to adjust the visualization component 1150. As the user rocks the ultrasound device 1150 within the aperture to align the visualization component along the angle of the target follicle, the extraction module is rotated about the pivot member 1105 such that the extraction axis 1105 remains aligned with the visualization axis 1109. Once the user has identified the target follicle and has aligned the visualization axis 1109 to the appropriate angle for follicular extraction, the user may actuate the coring and clipping mechanism by applying a force to trigger 2016. The extraction module 2104 may advance to the engaged position to core and clip the target follicle. The user may then release the trigger 2016 to draw the coring and clipping cannulas from the surrounding tissue back to the first position. As the coring and clipping cannulas are drawn back into the housing, they may draw the clipped follicular unit from the surrounding tissue. The housing element may include an extraction port that is in communication with a suction tube 2021, which may be similar to tubing 16 that facilitates tissue removal along a tissue removal pathway. As the extraction module 2104 returns to the first position, the clipped follicular unit may become loose within the extraction module 2104, and thus susceptible to being pulled from the extraction module 2104 by suction. The clipped follicular unit may be drawn into the extraction port and along the tissue removal pathway.

The tubing may be connected to an external tissue preservation reservoir or isolation container, such as isolation container 28 described previously. The tubing may also be in communication with the motor unit 1101 to provide suction at the suction port within the extraction module, and to pull the removed tissue away from the site of extraction.

Figure 43:
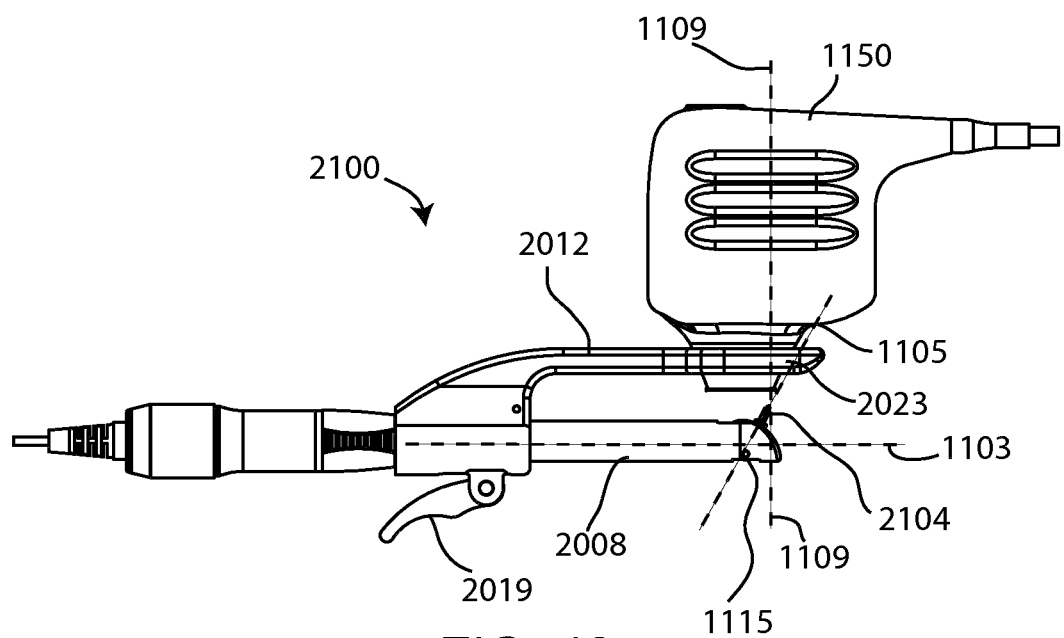
FIG. 43 is a side view of the instrument of FIG. 42.

Referring to FIGS. 42 and 43, another example of an instrument for hair follicle removal is shown. Instrument 2100 may have similar or identical features to instrument 2000. In this example, elongated prong 2012 does not include a rounded end portion, but rather, extends entirely parallel to second arm 2008. The visualization component 1105, which may also be a rod, pin, or other external reference device may be mounted on a flat end portion 2023 of elongated prong 2012, and may be linearly moveable on the end portion 2023 within an aperture or other receiving feature. In this example, the central visualization axis 1109 may be fixed in a perpendicular orientation to the longitudinal axis 1103 of second arm 2008. The extraction module 2104 may be coupled to the visualization component 1150 in a similar manner to instrument 2000.

Alternatively, the movement of the visualization component 1150 may be uncoupled from, or independent of, the rotation of the extraction module 2104. The visualization component 1150 may be manipulated directly, or via a toggle (not shown) by an operator to identify and gather information about a target follicular unit. After a target follicular unit has been identified, a user may then rotate the extraction module about pivot component 1115 by actuating trigger 2019, which may be connected to a cable, rod, or shaft (not shown). As the trigger 2019 is actuated, the cable or rod may provide a torque to the extraction module 2104 in order to align and activate the extraction module 2104 to core and clip the target follicular unit.

The system described herein may be used in any plastic surgery or dermatologic procedure that would otherwise require incision of the skin to reach a tissue of interest beneath the skin, such as a cancerous lesion. The system described herein allows an operator to obtain a tissue of interest beneath the skin surface without altering the skin surface that lies immediately above the tissue. The operator can effectively include the complete and intact tissue of interest due to effective visualization and delicate manipulation of the extracting module.

Utilizing the visualization technology provided by, for example, ultrasonography that enables the operator to simultaneously see both the underlying extraction module and the entire hair follicle that rests within the skin surface, the operator is better able manipulate the angle and direction of the device in order to align it properly with the overlying hair follicle that it will engage. Further, for hair follicle harvesting for subsequent transplantation, the system can described herein can include a larger amount of vital tissue structure around the hair follicle during extraction, which will enhance follicle viability and survival. During procedures where permanent hair follicle extraction is desired, such as from axillary and pelvic regions, the system may allow the removal of all of the hair follicle structure required for self-renewal to prevent unwanted hair regrowth.

Other advantages of the system described herein include the reduction or elimination of residual scarring, elimination of the need for a patient to shave their head in preparation for the procedure, reduction of recovery time and discomfort, decrease in the incidence of infection, and decreased trauma to the underlying vasculature. Further, this procedure is available and appropriate for a larger patient population, as patients with same-color hair and skin, curly hair, and those who do not wish to shave their heads are now candidates for hair follicle harvesting.

The invention claimed is:

1. A system, comprising:
 a body, wherein the body comprises a handle portion, a bridging component and a distal arm, wherein the bridging component is between the handle portion and the distal arm;
 a dissection module configured to dissect a plane of sub-follicular subcutaneous tissue, creating a layer of separation deep to the follicular bulbs, the dissection module being removably coupled to the body, the dissection module comprising a tissue separating device;
 an extraction module, wherein the extraction module comprises a coring component, at least one cutting feature, and at least one tissue removal port, wherein the tissue removal port is carried by the distal arm, wherein the extraction module comprises a central extraction axis; and,
 a dermal shifter actuatable to align a target tissue with the central extraction axis, the dermal shifter operably associated with the extraction module.

2. The system of claim 1, wherein the system further comprises an external reference module.

3. The system of claim 2, wherein the external reference module is external to an exterior tissue surface when the extraction module is in a subcutaneous cavity.

4. The system of claim 2, wherein the external reference module is communicably attached to the extraction module.

5. The system of claim 1, wherein the external reference module is a visualization component, wherein the visualization component comprises a central visualization axis.

6. The system of claim 5, wherein the central visualization axis is always aligned with the central extraction axis.

7. The system of claim 5, wherein the visualization component comprises at least one of an ultrasound device and a pointed rod.

8. The system of claim 1, wherein the removal port comprises a portion of a tissue removal pathway, wherein the tissue removal pathway is in fluid communication with a tissue reservoir.

9. The system of claim 1, wherein the dissection module is maneuverable to separate tissue layers to create a cavity.

10. The system of claim 1, wherein the extraction module is maneuverable within the cavity along an interior tissue surface.

11. The system of claim 1, wherein the extraction module is configured to subcutaneously extract a hair follicle.

12. The system of claim 1, wherein the system comprises an extraction trigger and an alignment adjuster, wherein the alignment adjuster is carried by a cable that is in communication with the extraction module, wherein when the alignment adjuster is actuated, the central extraction axis is pivotable about a first axis to align with a target tissue, wherein when the extraction trigger is actuated, the extraction module removes the target tissue along the tissue removal pathway.

13. The system of claim 1, wherein the dermal shifter comprises a plurality of needles that are actuatable to align a target tissue with the central extraction axis.

14. The system of claim 1, wherein the system comprises a plurality of independently controllable tissue removal implements, wherein each tissue removal implement is coupled to a corresponding suction port.

15. The system of claim 1, wherein the coring component is adapted for insertion through an incision and operator-driven movement upwards towards the target tissue.

16. A system, comprising:
- a body, wherein the body comprises a handle portion, a bridging component and a distal arm, wherein the bridging component is between the handle portion and the distal arm;
- a dissection module configured to dissect a plane of sub-follicular subcutaneous tissue, creating a layer of separation deep to the follicular bulbs, the dissection module being removably coupled to the body, the dissection module comprising a tissue separating device;
- an extraction module, wherein the extraction module comprises a coring component, at least one cutting feature, and at least one tissue removal port, wherein the tissue removal port is carried by the distal arm, wherein the extraction module comprises a central extraction axis; and,
- a visualization component that includes a central visualization axis, the visualization component communicably attached to the extraction module, wherein the visualization component comprises an ultrasound device, and wherein the central visualization axis is always aligned with the central extraction axis.

17. The system of claim 16, wherein the coring component is adapted for insertion through an incision and operator-driven movement upwards towards the target tissue.

18. The system of claim 16, wherein the visualization component is removably attached to the extraction module.

19. The system of claim 16, wherein the extraction module is configured to subcutaneously extract a hair follicle.

20. The system of claim 16, further comprising a dermal shifter actuatable to align a target tissue with the central extraction axis, the dermal shifter operably associated with the extraction module.

* * * * *